(12) United States Patent
Gregg et al.

(10) Patent No.: US 8,334,727 B2
(45) Date of Patent: Dec. 18, 2012

(54) MICROWAVE CAVITY SENSOR

(75) Inventors: John Francis Gregg, Oxford (GB); Mazhar Bari, Dublin (IE)

(73) Assignee: Isis Innovation Limited, Oxford (GB)

( * ) Notice: Subject to any disclaimer, the term of this patent is extended or adjusted under 35 U.S.C. 154(b) by 22 days.

(21) Appl. No.: 12/934,590

(22) PCT Filed: Mar. 27, 2009

(86) PCT No.: PCT/GB2009/050302
§ 371 (c)(1),
(2), (4) Date: Dec. 13, 2010

(87) PCT Pub. No.: WO2009/118569
PCT Pub. Date: Oct. 1, 2009

(65) Prior Publication Data
US 2011/0109406 A1    May 12, 2011

(30) Foreign Application Priority Data

Mar. 27, 2008    (GB) .................................. 0805571.7

(51) Int. Cl.
*H03B 7/12*        (2006.01)
*G01F 1/56*        (2006.01)
*G01P 5/08*        (2006.01)
*G01R 27/22*       (2006.01)
*H01P 7/06*        (2006.01)

(52) U.S. Cl. ................. 331/96; 331/107 DP; 73/861.08; 324/634; 324/636; 324/640; 324/643; 333/231

(58) Field of Classification Search ............ 331/96, 331/107 DP; 73/861, 861.08, 861.09, 861.11, 73/861.12, 861.16; 324/324, 629, 633, 634, 324/636, 639, 640, 643; 333/219, 227, 230, 333/231

See application file for complete search history.

(56) References Cited

U.S. PATENT DOCUMENTS 3,516,015 A * 6/1970 Hines et al. ................... 331/96
(Continued)

FOREIGN PATENT DOCUMENTS

WO        01/88513 A1    11/2001
(Continued)

OTHER PUBLICATIONS

Mulhausen, Dorothee; International Preliminary Report on Patentability (PCT/GB2009/050302);Sep. 28, 2010; 6 pgs;The International Bureau of WIPO; Geneva, Switzerland.

*Primary Examiner* — Levi Gannon
(74) *Attorney, Agent, or Firm* — Crain, Caton & James

(57) ABSTRACT

Apparatus comprising: a radio frequency (RF) Robinson oscillator comprising: a resonator comprising a sensor rhumbatron, the sensor rhumbatron comprising a cavity member, the cavity member having a re-entrant boss member, the re-entrant boss member being arranged to project into a cavity portion of the cavity member; a feedback element arranged to provide positive radio frequency (RF) feedback to the cavity member thereby to increase a quality factor Q of the cavity member, the feedback element having first and second terminals coupled to the cavity member, the apparatus being operable to cause the oscillator to oscillate at a resonant frequency; and an output arranged to provide a signal that varies according to a value of at least one electrical parameter of the oscillator, said at least one electrical parameter being selected from amongst an electromagnetic loss and a resonant frequency.

20 Claims, 20 Drawing Sheets

U.S. PATENT DOCUMENTS

| | | | |
|---|---|---|---|
| 3,769,623 A | 10/1973 | Fletcher et al. | |
| 4,730,169 A * | 3/1988 | Li | 331/36 C |
| 5,260,665 A * | 11/1993 | Goldberg et al. | 324/636 |
| 5,837,926 A | 11/1998 | Franklin | |
| 6,466,035 B1 * | 10/2002 | Nyfors et al. | 324/634 |
| 6,879,166 B2 * | 4/2005 | May et al. | 324/636 |

FOREIGN PATENT DOCUMENTS

| | | |
|---|---|---|
| WO | 02/01211 A1 | 1/2002 |

\* cited by examiner (a)

(b)

(a)

(b)

MICROWAVE CAVITY SENSOR

FIELD OF THE INVENTION

The present invention relates to microwave cavities. In particular but not exclusively the invention relates to a sensor comprising a re-entrant microwave cavity.

BACKGROUND

It is known to provide a microwave cavity in the form of a rhumbatron. A rhumbatron 10 is illustrated schematically in FIG. 1 where it can be seen to comprise a cavity member 12 and a re-entrant boss member 14. When coupled to a suitable source of radio frequency (RF) radiation the rhumbatron is capable of producing high voltages whilst requiring relatively little input power.

STATEMENT OF THE INVENTION

In a first aspect of the present invention there is provided apparatus comprising: a radio frequency (RF) Robinson oscillator comprising: a resonator comprising a sensor rhumbatron, the sensor rhumbatron comprising a cavity member, the cavity member having a re-entrant boss member, the re-entrant boss member being arranged to project into a cavity portion of the cavity member; a feedback element arranged to provide positive radio frequency (RF) feedback to the cavity member thereby to increase a quality factor Q of the cavity member, the feedback element having first and second terminals coupled to the cavity member, the apparatus being operable to cause the oscillator to oscillate at a resonant frequency; and an output arranged to provide a signal that varies according to a value of at least one electrical parameter of the oscillator, said at least one electrical parameter being selected from amongst an electromagnetic loss and a resonant frequency.

A Robinson oscillator is an oscillator having a nonlinearity in the feedback element in the form of a signal amplitude limiter in accordance with the Robinson principle. The limiter is a hard limiter (i.e. a 'clipper'); thus, when the amplitude of an input to the limiter exceeds a threshold limit value of the limiter, a level of an output of the limiter (which may correspond to an output of the feedback element) remains substantially constant until the amplitude of the input to the limiter falls below the threshold limit value. Provision of a feedback element having a nonlinear relationship between an input and an output of the feedback element has the advantage that an amplitude of oscillation of the oscillator may be limited in a predictable and controllable manner.

The quality factor Q of a resonator is defined as $2\pi$ multiplied by the energy stored per cycle of oscillation divided by the energy dissipated per cycle of oscillation.

In a second aspect of the invention there is provided apparatus comprising: a radio frequency (RF) oscillator comprising: a resonator comprising a sensor rhumbatron having a cavity member, the cavity member having a re-entrant boss member arranged to project into a cavity portion of the cavity member; a negative resistance element configured to exhibit negative resistance between first and second terminals of the element, the first and second terminals being coupled to the cavity member, the apparatus being operable to cause the oscillator to oscillate at a resonant frequency; and an output arranged to provide a signal that varies according to a value of at least one electrical parameter of the oscillator, said at least one parameter being selected from amongst an electromagnetic loss and a resonant frequency.

The first and second terminals of apparatus according to the first or second aspects may be coupled to the boss member and cavity member respectively.

Preferably the first and second terminals of the negative resistance element of the second aspect are coupled to the boss member and cavity member respectively at respective first and second positions whereby the impedance of the negative resistance element corresponds to an impedance of the cavity member between the first and second positions.

The negative resistance element may comprise a Gunn diode or a tunnel diode.

The tunnel diode may be an Esaki diode.

The negative resistance element may comprise a gain element arranged such that positive feedback is applied to an input thereof from an output thereof.

Preferably apparatus according to the first or second aspects is provided with means for introducing a target measurand into an interior of the cavity member.

Preferably the cavity member is provided with a fluid inlet and a fluid outlet, the apparatus being arranged whereby a fluid flow-path is provided through at least a portion of an interior of the cavity member between the fluid inlet and the fluid outlet.

In a third aspect of the invention there is provided apparatus comprising: a radio frequency (RF) oscillator comprising: a resonator comprising a sensor rhumbatron having a cavity member, the cavity member having a re-entrant boss member arranged to project into a cavity portion of the cavity member, the apparatus further comprising a feedback element arranged to provide positive radio frequency (RF) feedback to the cavity member thereby to increase a quality factor Q of the cavity member, the feedback element having first and second terminals coupled to the cavity member, the apparatus being operable to cause the oscillator to oscillate at a resonant frequency; and an output arranged to provide a signal that varies according to a value of at least one electrical parameter of the oscillator, said at least one parameter being selected from amongst an electromagnetic loss and a resonant frequency, wherein the cavity member is provided with a fluid inlet and a fluid outlet, the apparatus being arranged whereby a fluid flowpath is provided through at least a portion of an interior of the cavity member between the fluid inlet and the fluid outlet.

Apparatus according to any one of the first, second and third aspects may be configured whereby the first cavity member may be substantially filled with a fluid by forcing fluid through the first cavity member from the fluid inlet to the fluid outlet.

Preferably the fluid inlet and the fluid outlet are each provided by an aperture in a wall of the cavity member, a diameter of the aperture being arranged to be sufficiently small whereby the aperture provides a waveguide configured to function in a cut-off condition when the sensor rhumbatron is excited in use.

The fluid inlet and the fluid outlet of the oscillator may be provided on opposite sides of the cavity member.

The apparatus may be arranged whereby a direction of flow of fluid through the cavity member from the inlet aperture to the outlet aperture is substantially parallel to a longitudinal axis of the boss member.

The cavity member may be provided in a section of a pipe.

Preferably fluid flowing through the pipe is forced to pass through the cavity member.

Fluid flowing through the cavity member from the inlet to the outlet may be confined to a tube member provided between the inlet and the outlet, the tube member having a fluid capacity in a volume of the tube member between the inlet and outlet that is less than a fluid capacity of the cavity member.

Preferably the dielectric loss of the tube material is chosen to be sufficiently low that it does not significantly depress the quality factor of the cavity.

This has the advantage that where liquids of relatively high loss and/or relatively high dielectric constant are used a risk that oscillation of the cavity member is terminated upon introduction of the liquid into the tube or the resonant frequency shifted beyond the range in which electronic devices associated with the sensor function satisfactorily is reduced.

Preferably the tube member is formed from an insulating material.

The tube member may be formed from at least one selected from amongst a plastics material and a glass material.

The apparatus may further comprise a reference RF oscillator. The reference RF oscillator may have a reference resonator. The reference resonator may comprise a reference rhumbatron. The reference rhumbatron may have a reference cavity member. The reference cavity member may have a reference fluid provided therein. The reference oscillator may be operable to oscillate at a reference resonant frequency.

The reference fluid may be a gas such as air, an inert gas, a flammable gas such as a fuel gas, or any other suitable gas. The reference fluid may be a liquid, a gel, an emulsion of any other suitable fluid.

Alternatively a solid material may be provided in the reference cavity. The solid material may comprise a foam. In some embodiments the reference cavity comprises an evacuated cavity.

Preferably the apparatus is configured to provide an output corresponding to at least one selected from amongst a resonant frequency of the reference rhumbatron and an electromagnetic loss of the reference rhumbatron.

The apparatus may be configured to provide an output corresponding to at least one selected from amongst a difference between a resonant frequency of the sensor oscillator and a resonant frequency of the reference oscillator, and a difference between an electromagnetic loss of the cavity member of the sensor rhumbatron and an electromagnetic loss of the cavity member of the reference rhumbatron.

The apparatus may be arranged wherein a magnetic field may be applied to the cavity to enhance a sensitivity of the apparatus to detection of the target measurand.

The magnetic field may be arranged to induce Zeeman splitting of a prescribed target measurand.

Preferably the magnetic field is a modulated DC magnetic field.

The first and second terminals may be coupled to one another, the first and second terminals being coupled to the rhumbatron by means of a single coupler, preferably a single loop coupler or a single stub coupler.

Alternatively the first terminal may be coupled to the rhumbatron by means of at least one selected from amongst a loop coupler and a stub coupler and the second terminal may be coupled to the rhumbatron by means of at least one selected from amongst a loop coupler and a stub coupler.

The apparatus may be arranged to detect the presence of at least one selected from amongst liquid helium, liquid nitrogen, water, a Van Vleck paramagnet, a Curie Law paramagnet, a diamagnet, a thin ferromagnetic film or multilayer film by ferromagnetic resonance, a giant magneto resistive film or multilayer by ferromagnetic resonance, a ferromagnetic particle or assembly of particles, a superconductor and an electron spin resonance system.

In a fourth aspect of the invention there is provided an engine having apparatus according to any one of the preceding aspects arranged to detect a target measurand in an engine fluid.

In a fifth aspect of the invention there is provided a motor vehicle having an engine according to the fourth aspect of the invention.

In a sixth aspect of the invention there is provided a motor vehicle having apparatus according to any one of the first, second or third aspects arranged to detect a target measurand in a fluid associated with the vehicle.

The fluid may be brake fluid and the apparatus may be coupled to a brake fluid pipe of the vehicle whereby brake fluid is passed through a cavity portion of the apparatus thereby to detect the presence of a target measurand in the brake fluid.

The fluid may be engine coolant and the apparatus may be coupled to an engine coolant pipe of the vehicle whereby coolant is passed through a cavity portion of the apparatus thereby to detect the presence of a target measurand in the engine coolant.

The fluid may be liquid fuel and the apparatus may be coupled to a fuel pipe of the vehicle whereby fuel is passed through a cavity portion of the apparatus thereby to detect the presence of a target measurand in the liquid fuel. The fuel may be a gaseous fuel such as methane, ethane, butane, propane, oxygen, acetylene or any other gaseous fuel or mixture thereof. Other non-fuel gases are also useful.

The fluid may be engine oil and the apparatus may be coupled to an engine oil pipe of the vehicle whereby engine oil is passed through a cavity portion of the apparatus thereby to detect the presence of a target measurand in the engine oil.

The fluid may be automatic transmission fluid (ATF) and the apparatus may be coupled to an ATF pipe of the vehicle whereby ATF is passed through a cavity portion of the apparatus thereby to detect the presence of a target measurand in the ATF.

Embodiments of the invention will now be described with reference to the accompanying figures in which.

Figure 6:
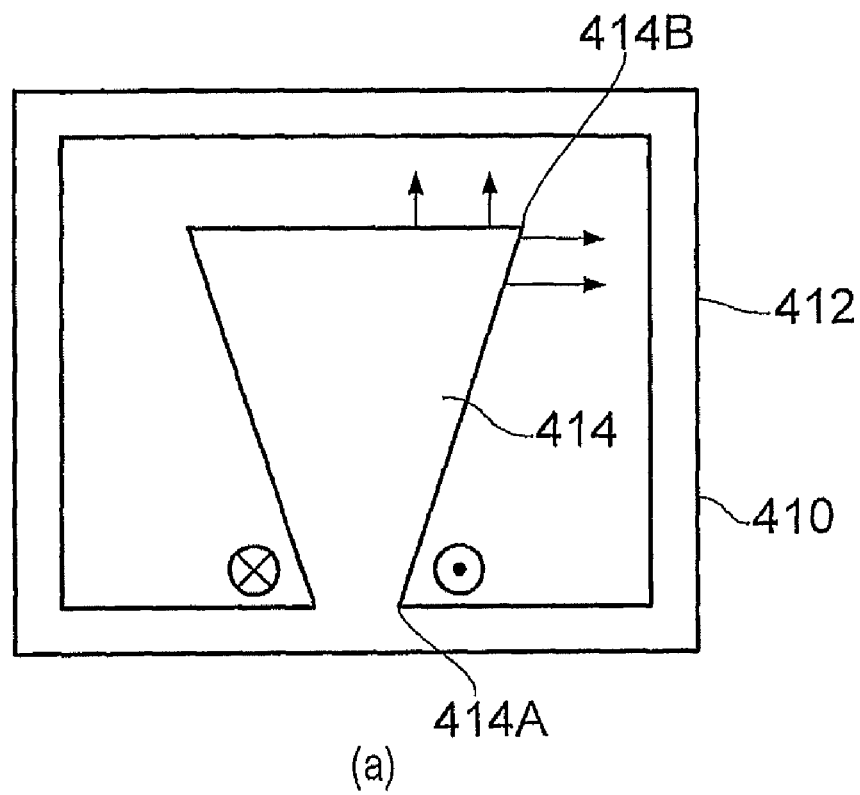
Figure 6:
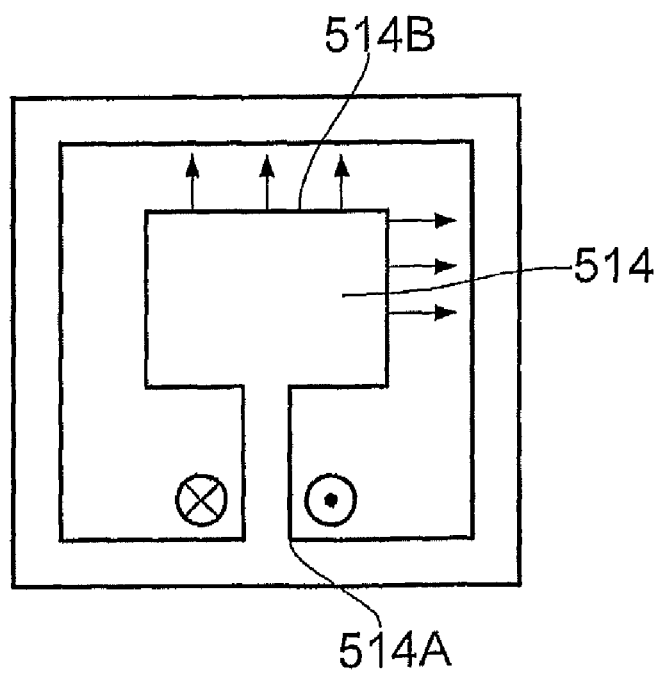
Figure 7:
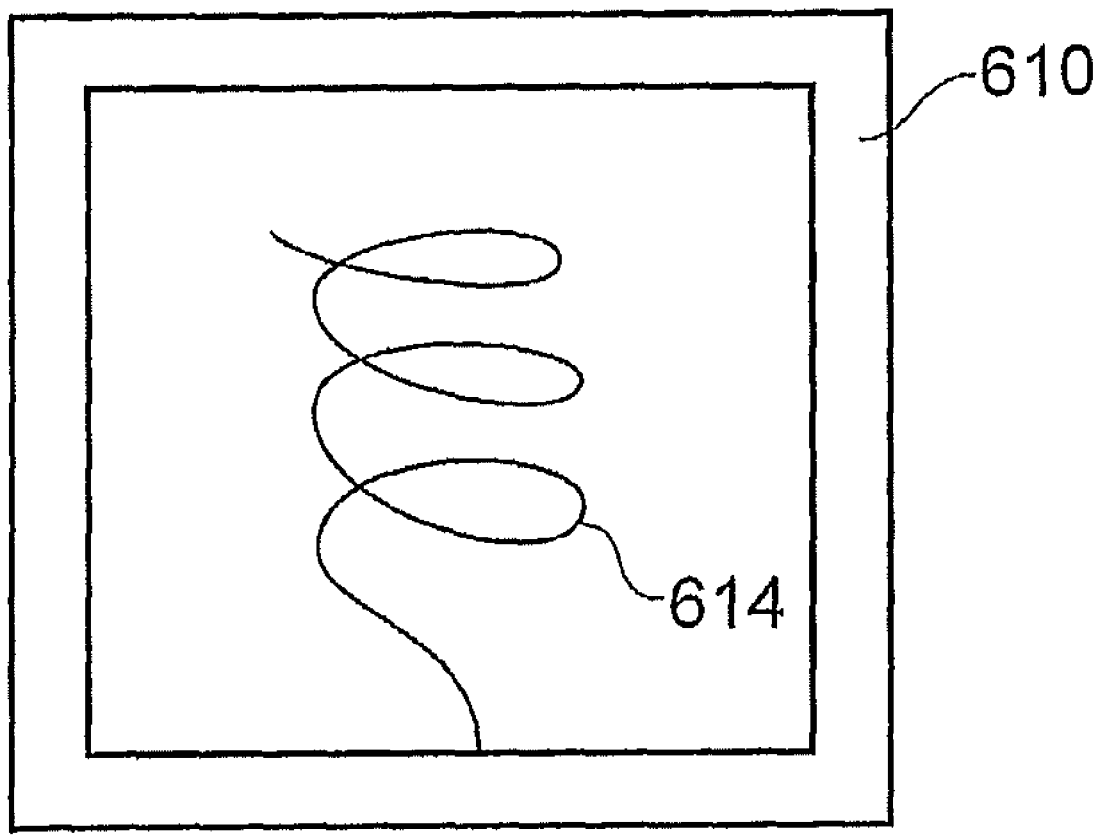
Figure 8:
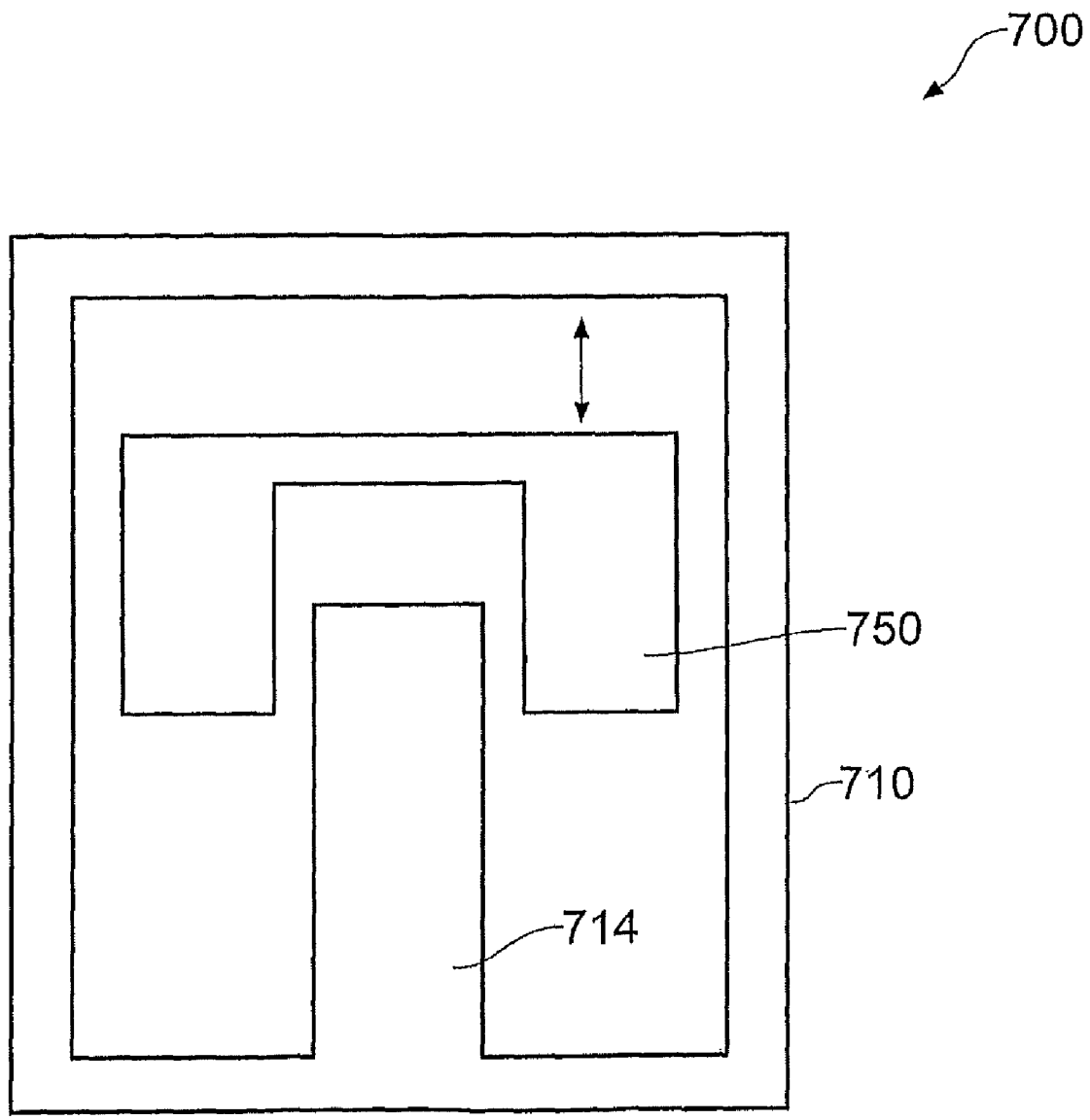
Figure 9:
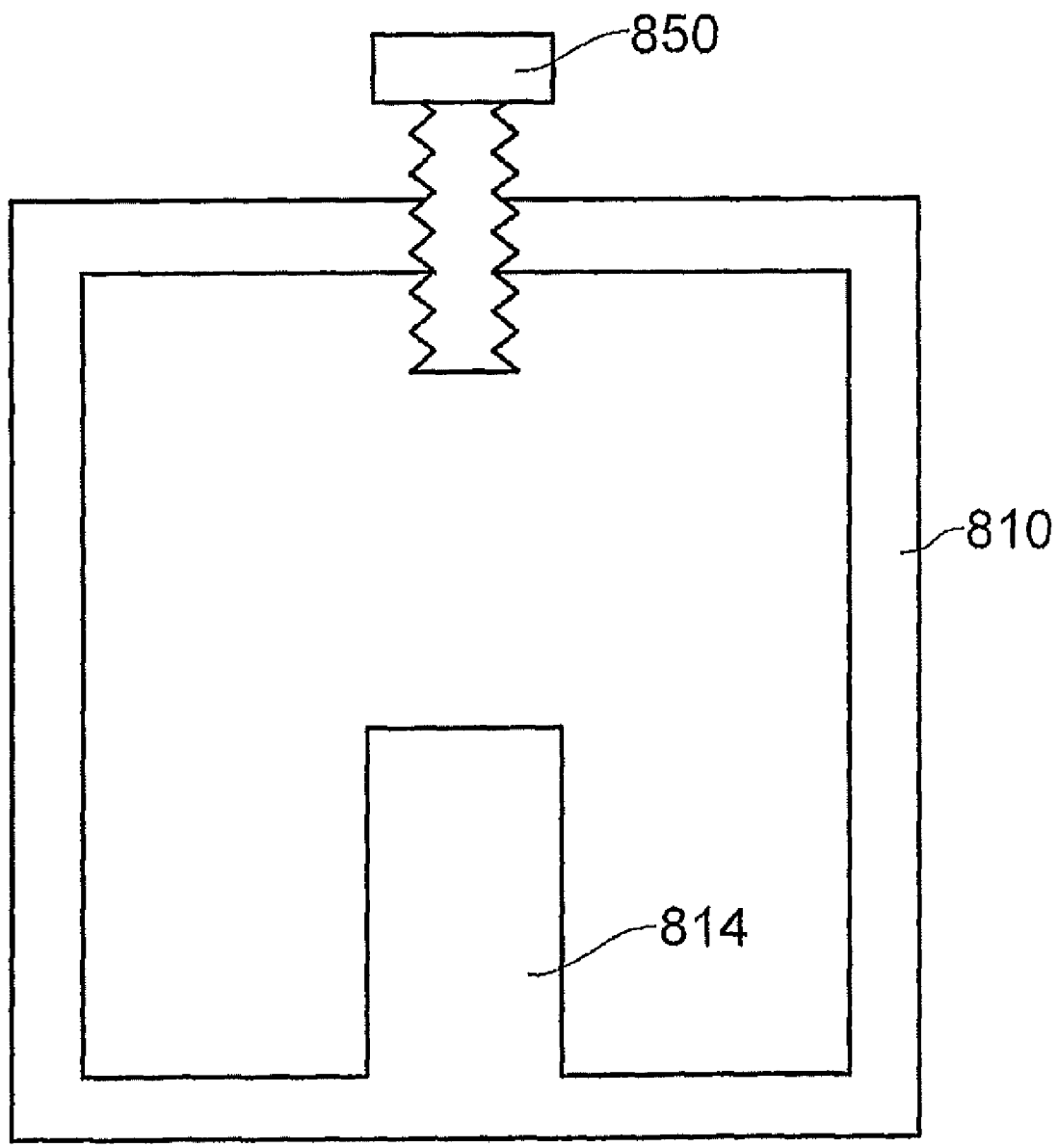
Figure 10:
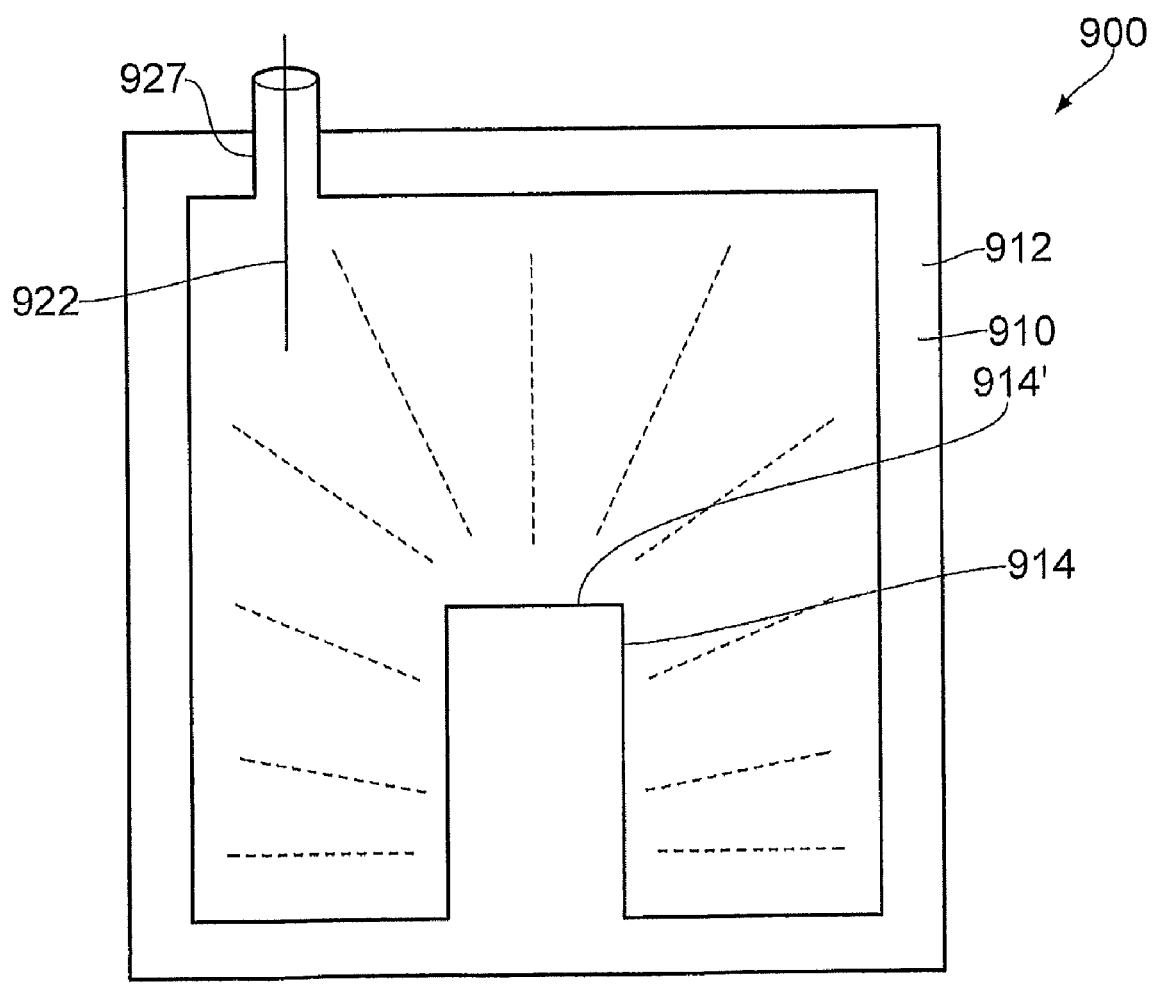
Figure 11:
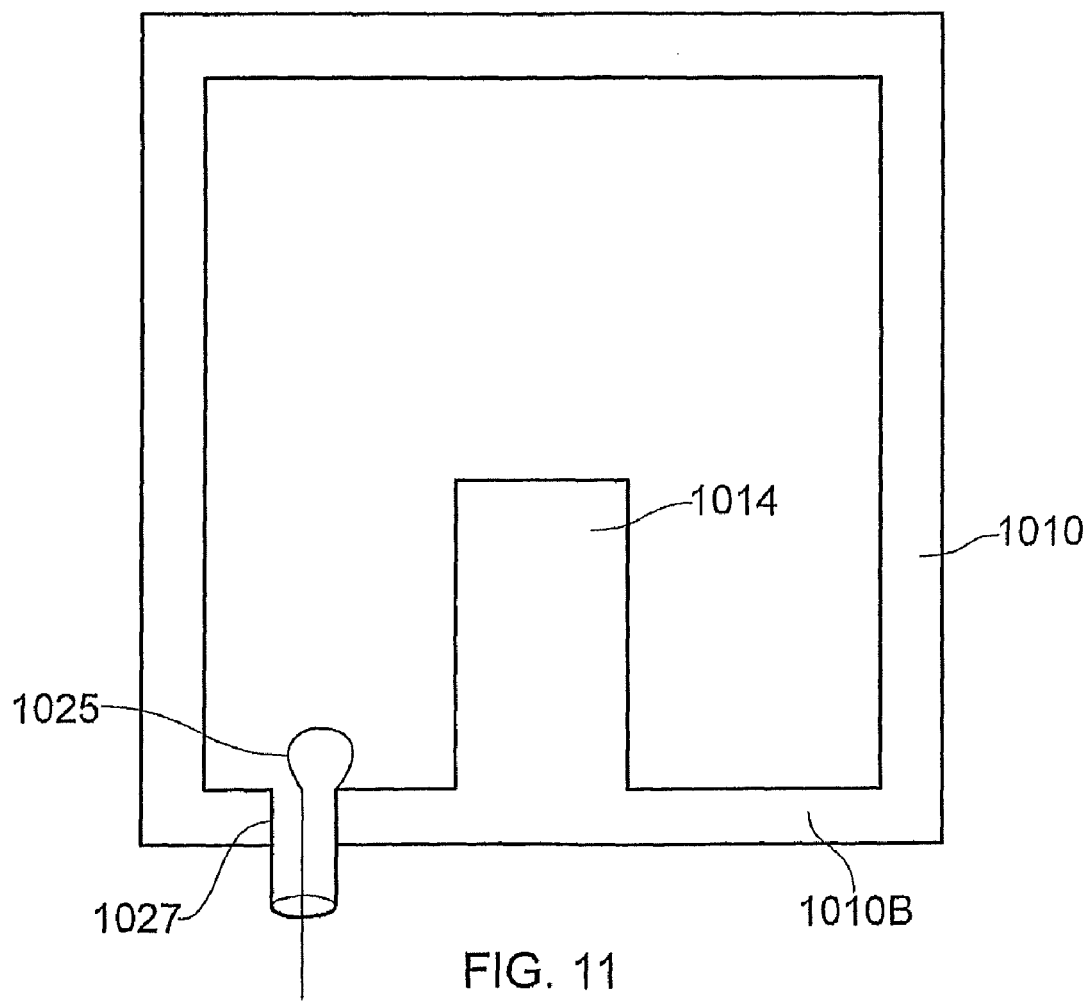
Figure 12:
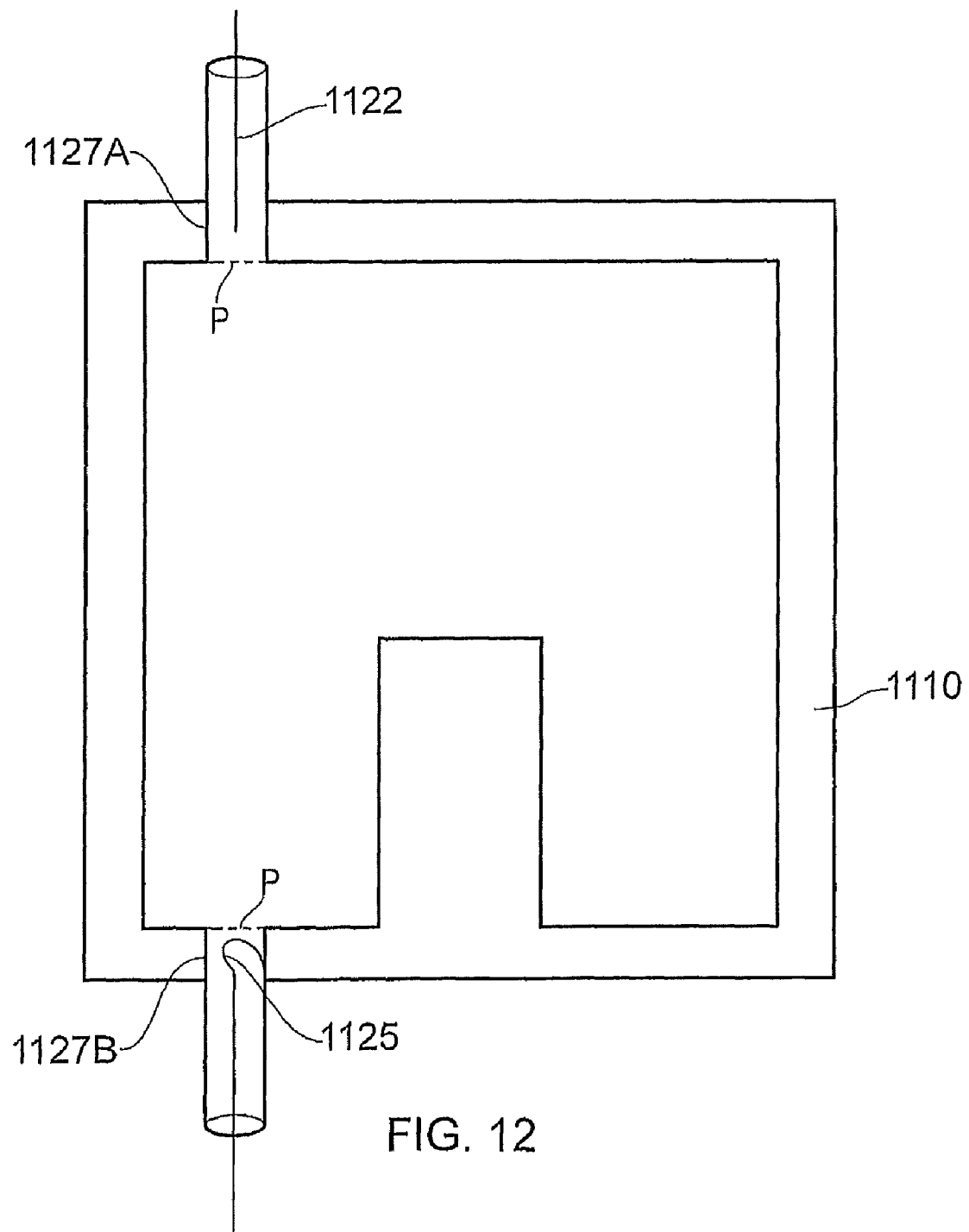
Figure 13:
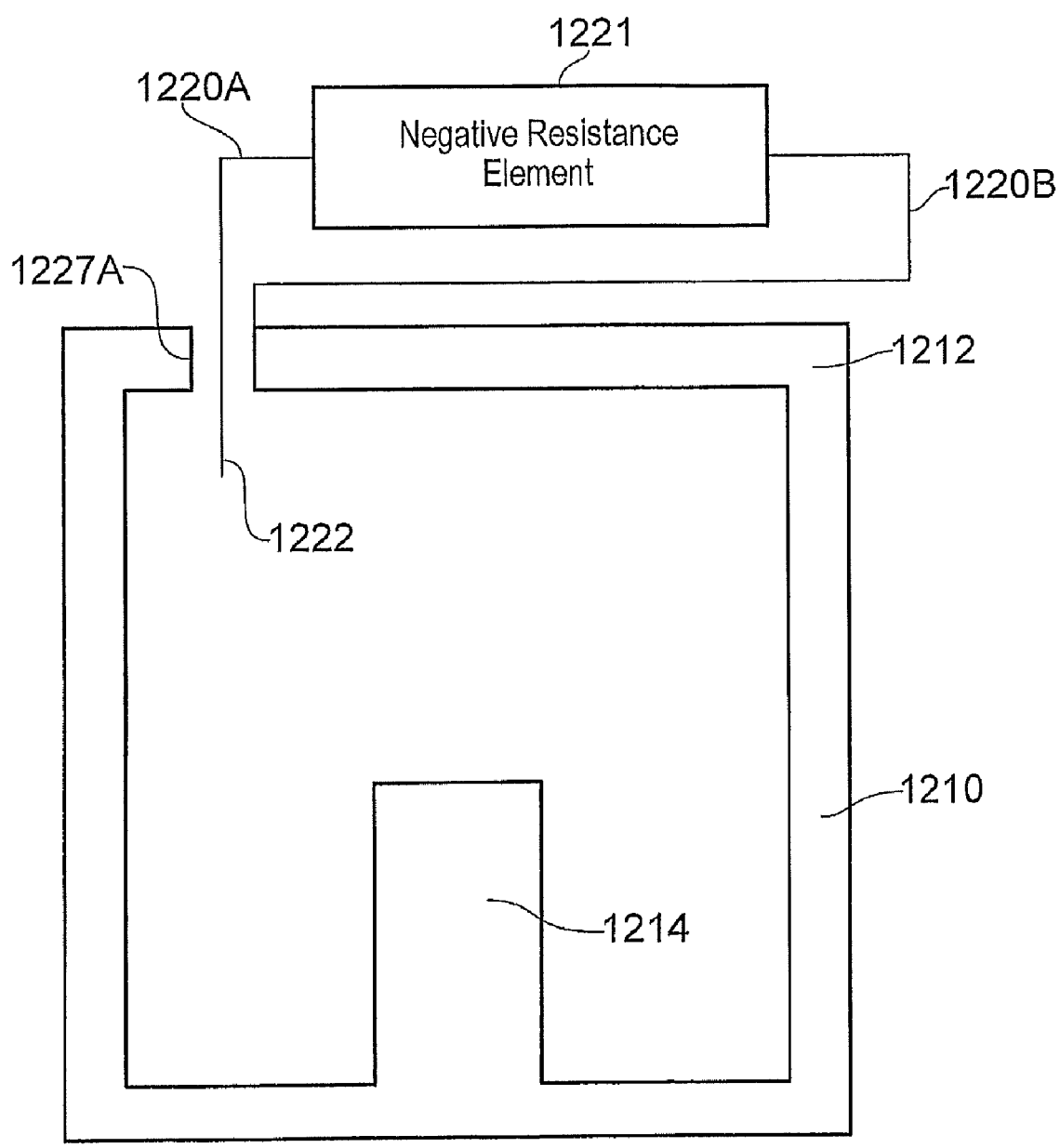
Figure 13A:
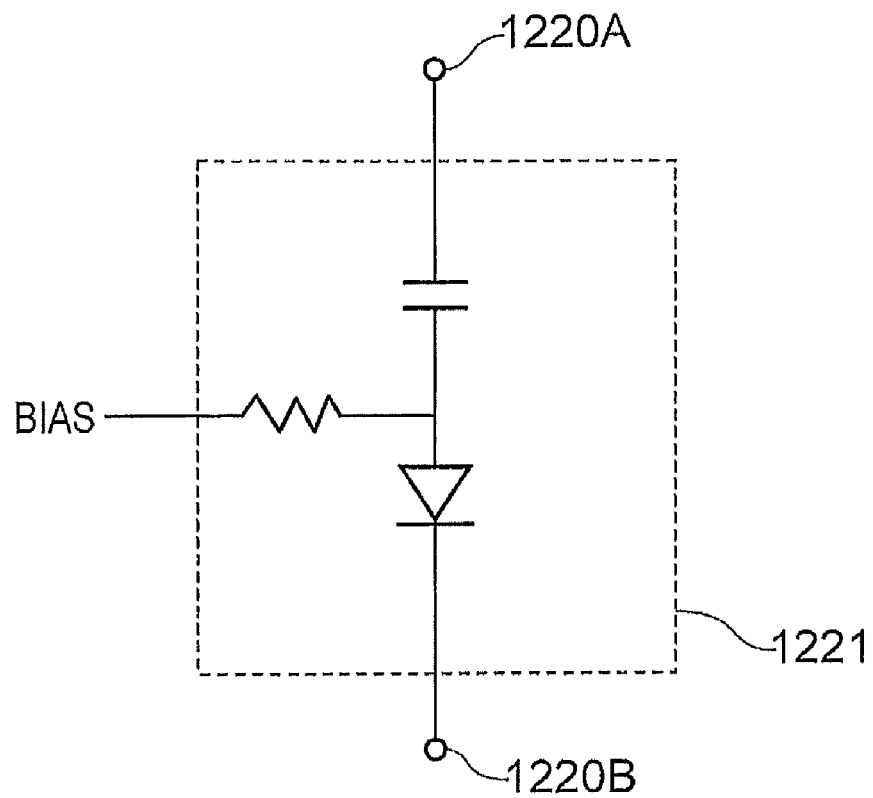
Figure 13B:
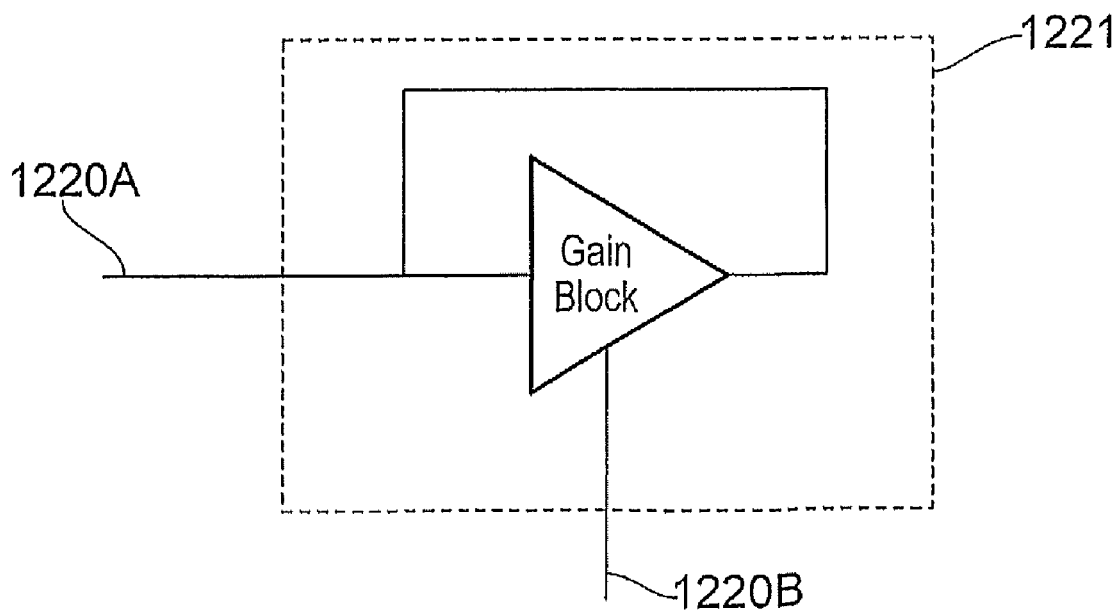
Figure 14:
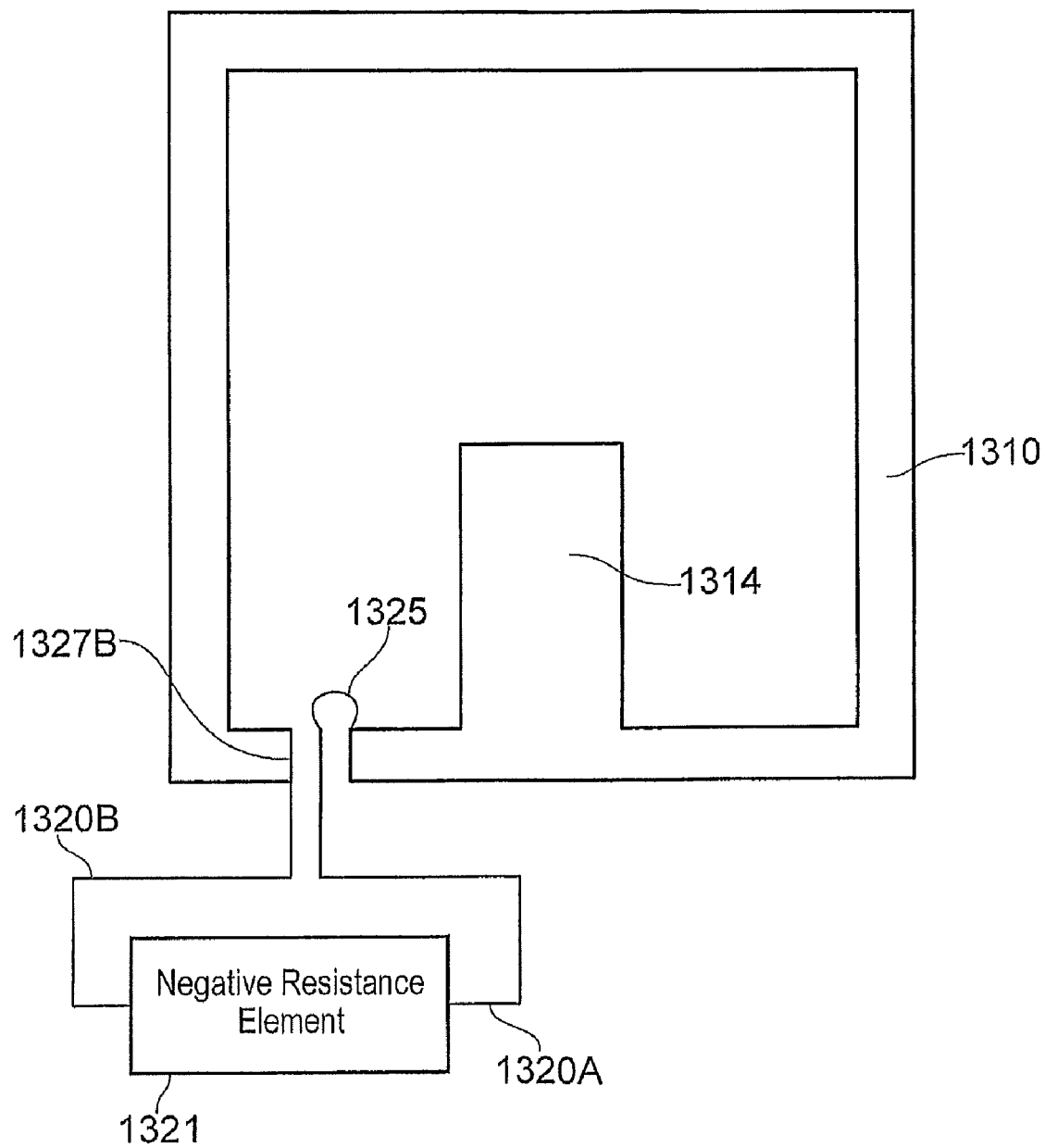
Figure 15:
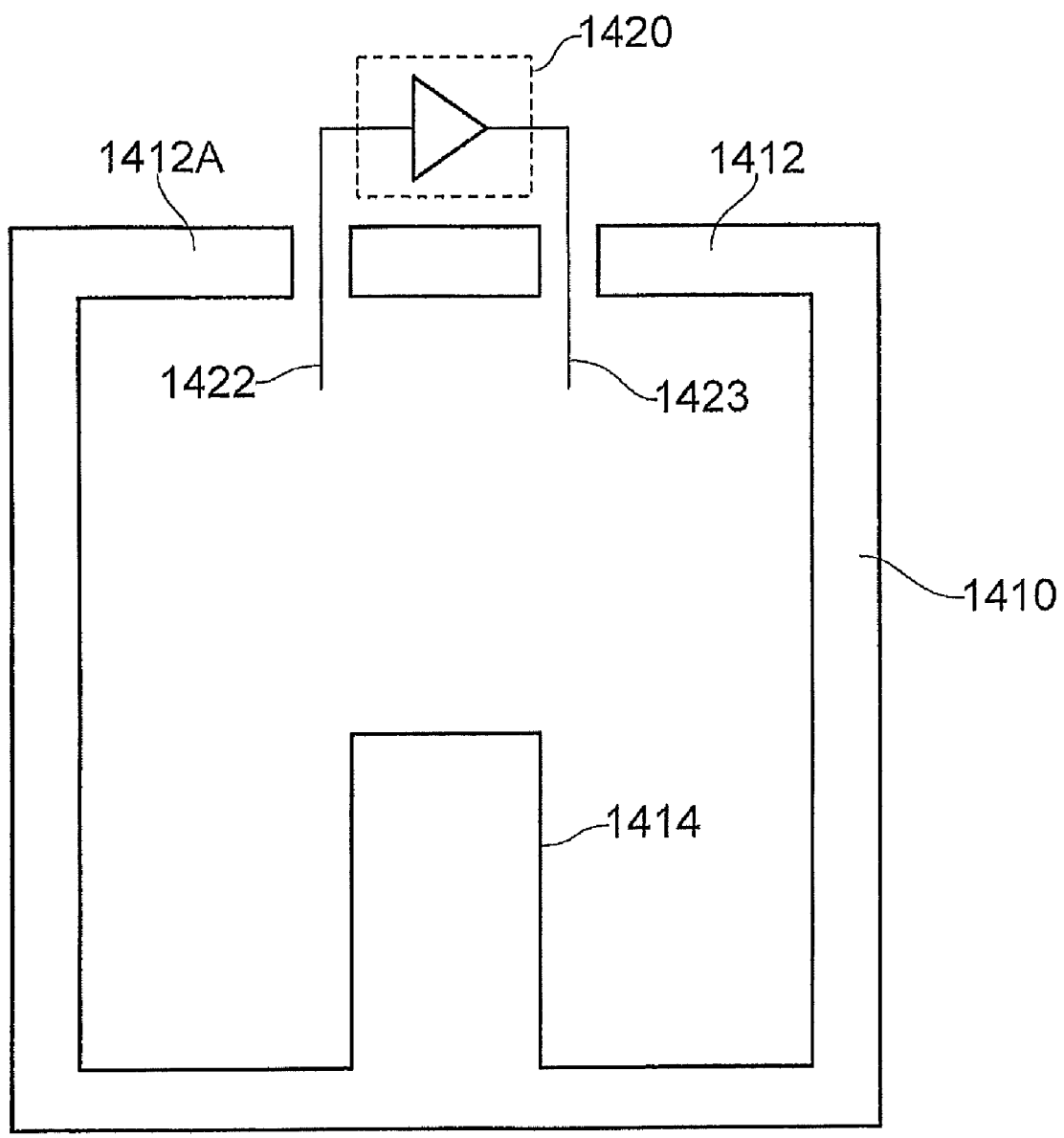
Figure 16:
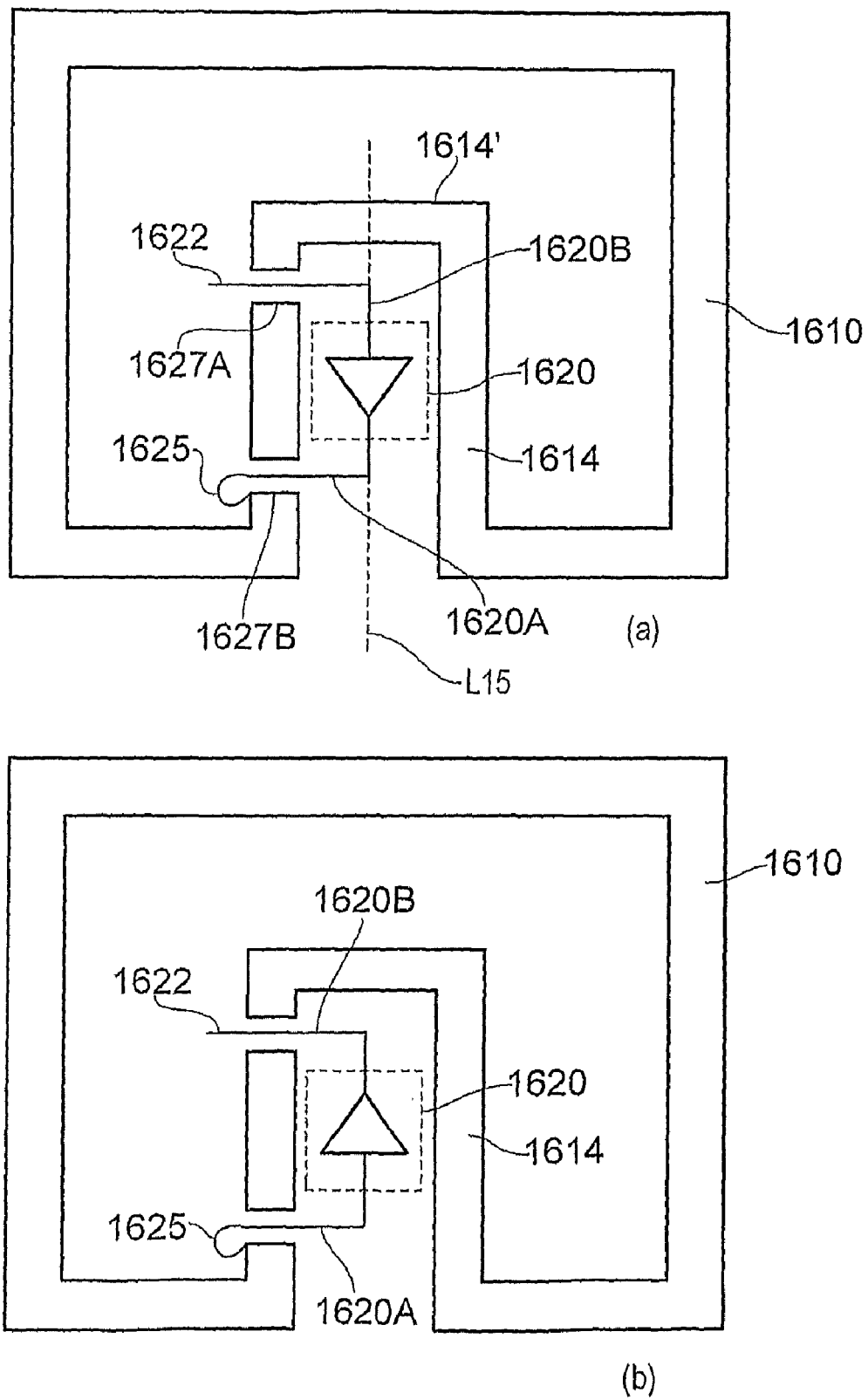
Figure 17:
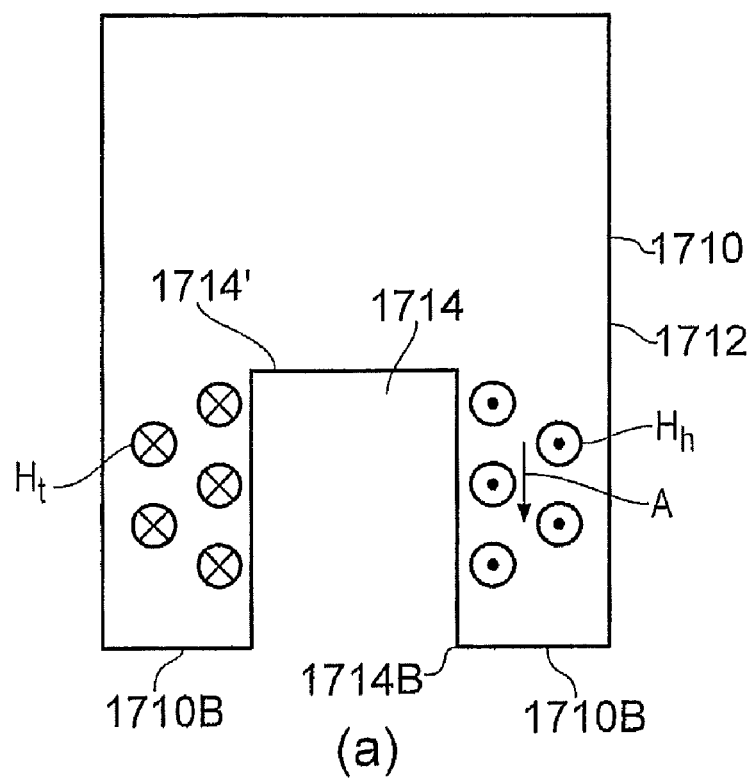
Figure 17:
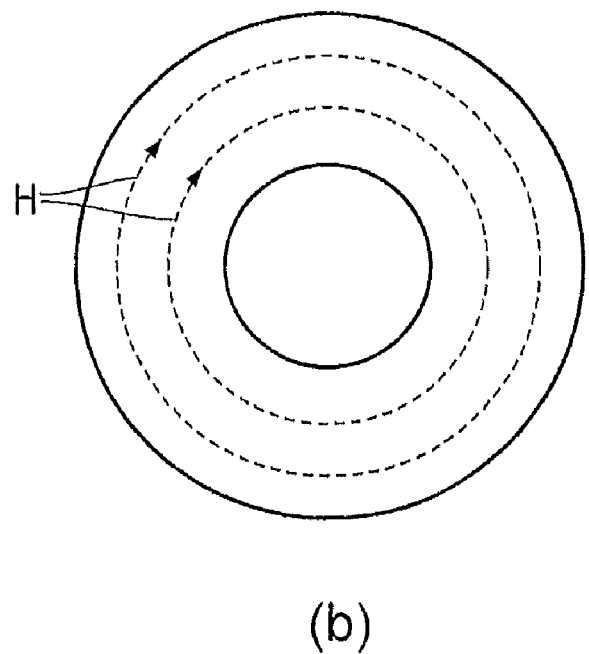
Figure 18:
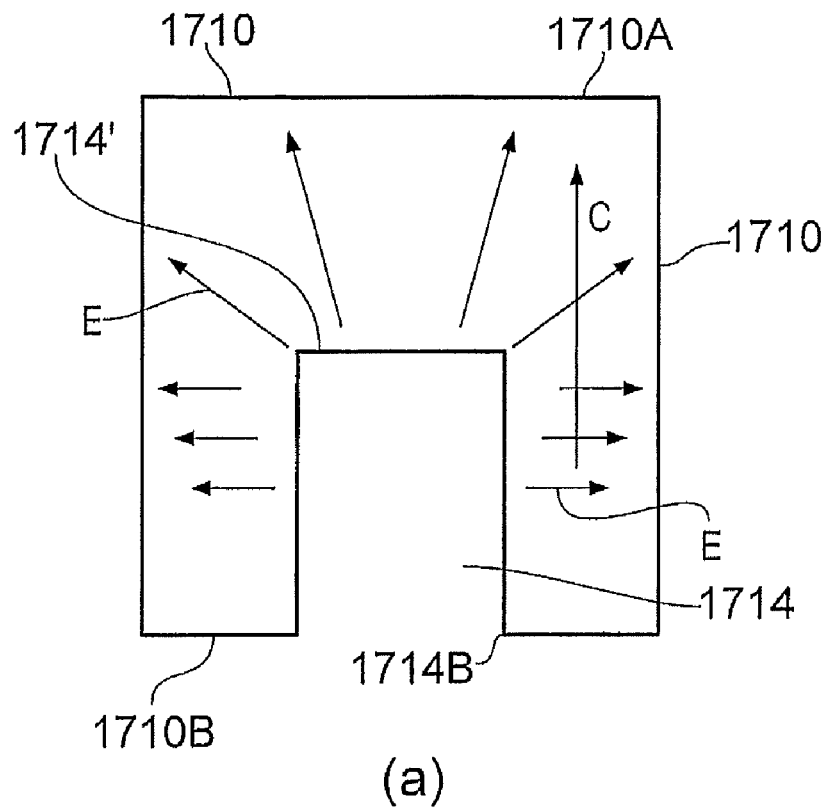
Figure 18:
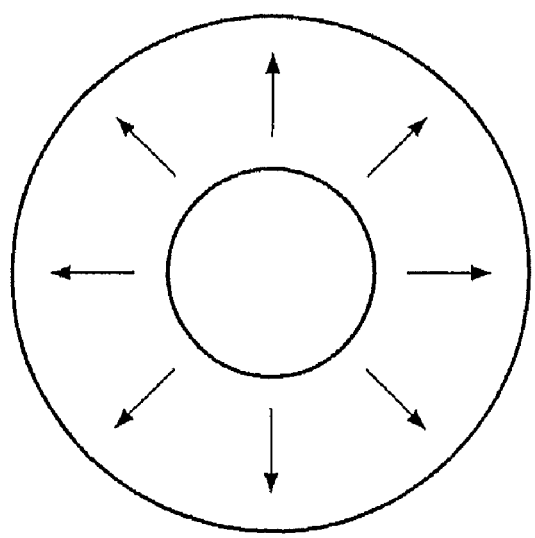
Figure 19:
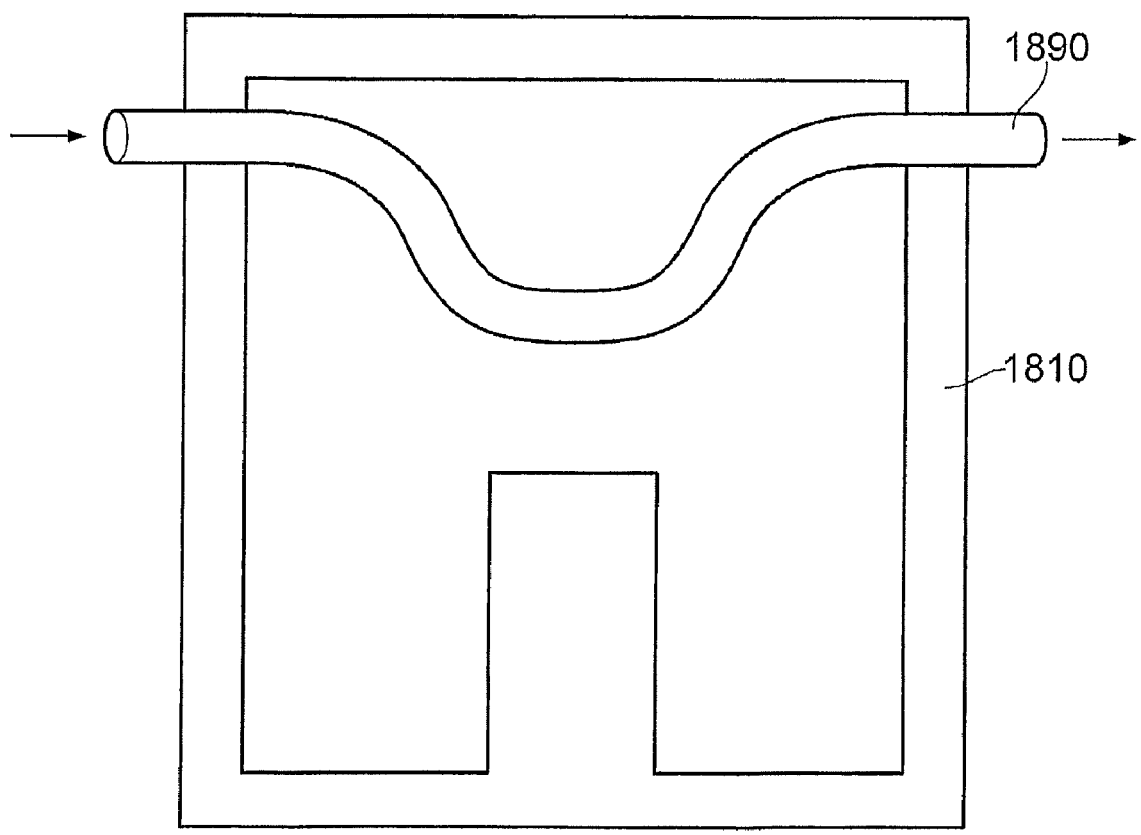

FIG. 6 (*a*) and (*b*) are schematic illustrations of rhumbatron cavity members having enhanced electric and magnetic fields;

FIG. 7 is a schematic illustration of a rhumbatron cavity member having a slow wave line boss member;

FIG. 8 is a schematic illustration of a tuneable rhumbatron cavity member;

FIG. 9 is a schematic illustration of a further tuneable rhumbatron cavity member;

FIG. 10 is a schematic illustration of a rhumbatron cavity member having a stub coupler;

FIG. 11 is a schematic illustration of a rhumbatron cavity member having an inductive coupler;

FIG. 12 is a schematic illustration of a rhumbatron cavity member having a retreated stub coupler and a retreated inductive coupler;

FIG. 13 is a schematic illustration of a rhumbatron cavity member having single stub coupler excitation;

FIGS. 13A and 13B show negative resistance elements employed in some embodiments of the invention FIG. 14 is a schematic illustration of a rhumbatron cavity member having single inductive coupler excitation;

FIG. 15 is a schematic illustration of a rhumbatron cavity member having dual stub coupler excitation;

FIG. 16 (a) and (b) are schematic illustrations of a rhumbatron cavity member having single stub coupler and inductive coupler excitation;

FIG. 17 (a) and (b) are schematic illustrations showing magnetic field lines within a rhumbatron cavity member;

FIG. 18 (a) and (b) are schematic illustrations showing electric field lines within a rhumbatron cavity member; and FIG. 19 shows an embodiment of the invention in which a pipe is provided as a fluid conduit through the cavity portion between a fluid inlet and a fluid outlet.

DETAILED DESCRIPTION

Figure 1A:
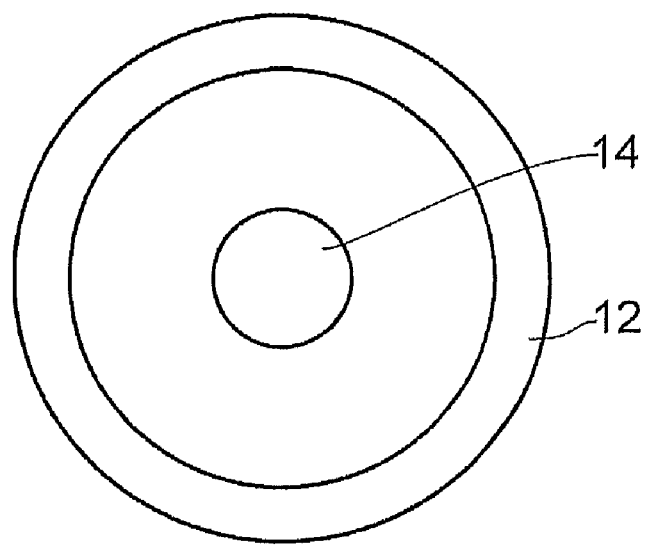
FIG. 1 shows a known rhumbatron microwave cavity.
Figure 1B:
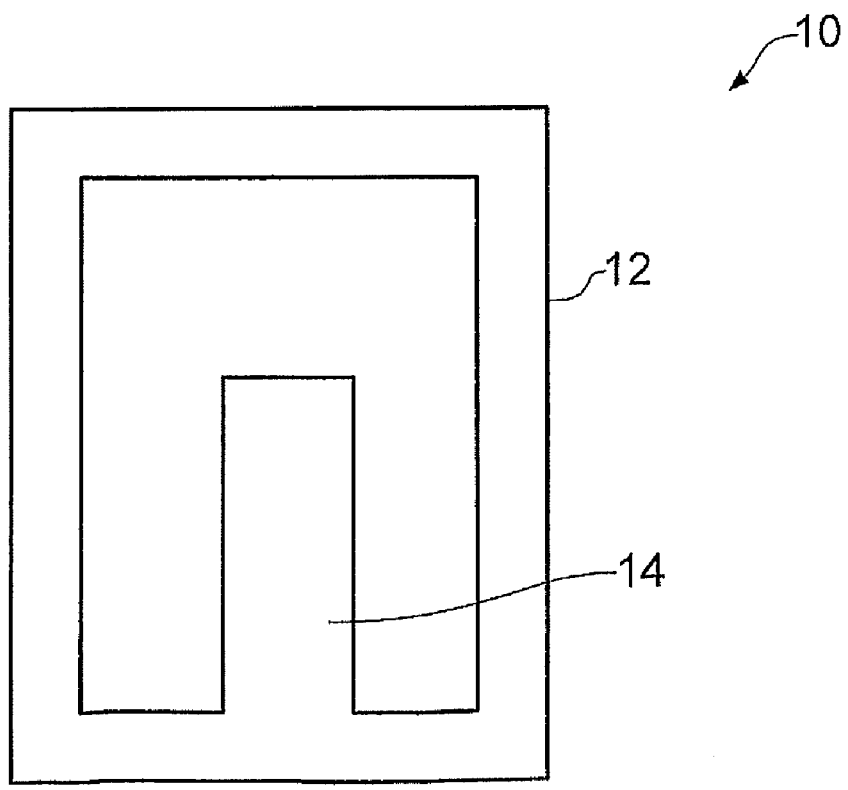
Figure 2:
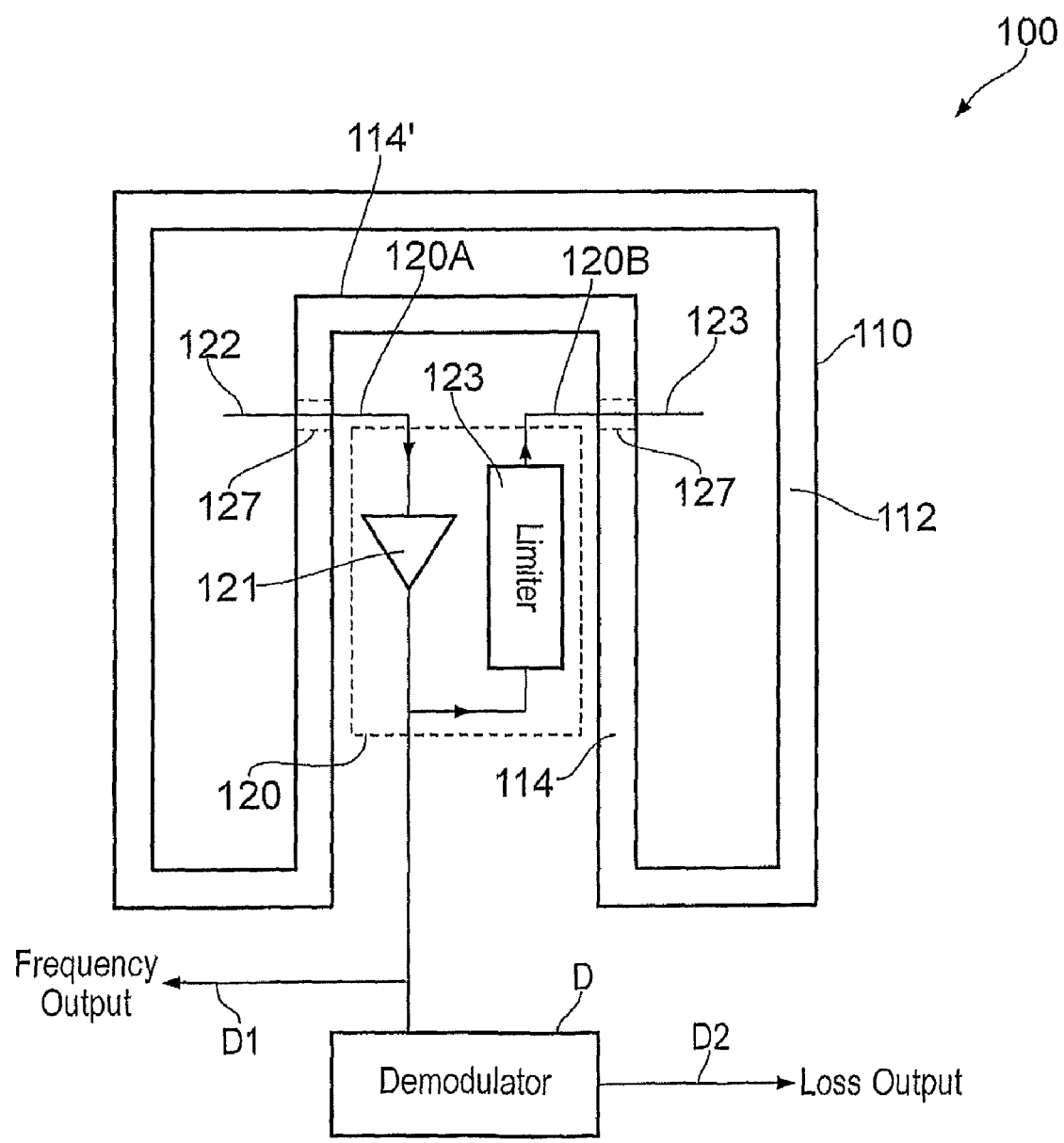
FIG. 2 shows a rhumbatron cavity having a nonlinear positive feedback member.

In one embodiment of the invention a sensor 100 is provided as shown in FIG. 2. The sensor 100 has a microwave cavity oscillator circuit.

The sensor 100 has a rhumbatron cavity member 110 having a cavity portion 112 and a re-entrant boss portion 114. The cavity portion 112 is configured such that a target measurand may be introduced into the cavity portion 112.

A positive feedback module 120 is provided having a radio frequency (RF) amplifier 121 coupled in series with a limiter 123, the feedback module 120 having an input 120A and an output 120B. Input 120A and output 120B are coupled electrically to the cavity member 110 by means of stub couplers 122, 123. The stub couplers 122, 123 are disposed to pass through apertures 127 formed in a wall of the re-entrant boss portion 114 of the cavity member 110 at a location proximate a free end 114' of the boss portion 114. In the embodiment shown in FIG. 2 the boss portion 114 is substantially in the form a cylinder and apertures 127 are provided in the boss portion 114 at diametrically opposed locations.

Other arrangements of inductive couplers are also useful. Other types of coupler may be used instead of or in addition to inductive couplers, such as stub couplers.

The RF amplifier 121, limiter 123 and cavity member 110 are arranged to provide a Robinson marginal oscillator circuit operating according to the Robinson principle.

The limiter is a hard limiter (i.e. a 'clipper'); thus, when the amplitude of an input exceeds a threshold limit value of the limiter 123, a level of an output remains substantially constant until the amplitude of the input falls below the threshold limit value.

In some embodiments of the invention apparatus that includes a sensor 100 is arranged to detect the presence of a target measurand by detecting a change in resonant frequency of the oscillator circuit. In some embodiments, the output of the feedback module 120 is arranged to provide an output corresponding to the resonant frequency of the oscillator circuit. In some embodiments the feedback module 120 is arranged to provide an output corresponding to an amount of electromagnetic loss of the cavity member 110.

In the embodiment of FIG. 2 a demodulator module D is coupled to the feedback module 120 at a location between the RF amplifier 121 and limiter 123. The demodulator module is arranged to provide an output D1 corresponding to a frequency of oscillation of the cavity member 110 and an output D2 corresponding to an amount of electromagnetic loss of the cavity member 110. The demodulator may be configured according to the Robinson principle.

Other methods of measuring the frequency of oscillation and/or electromagnetic loss are also useful.

In some embodiments the RF signal provided at output D1 is rectified and the resulting DC signal monitored to determine the amplitude of RF radiation in cavity member 110.

In some embodiments the cavity member 110 has a fluid inlet and a fluid outlet arranged to allow fluid to pass into and out from the cavity member 110. In some embodiments the fluid inlet and fluid outlet are provided by apertures in a wall of the cavity member 110. In some embodiments the apertures are of a size sufficiently small whereby they act as waveguides configured beyond cut-off, thereby limiting an amount of RF radiation that can pass through (or 'leak') through the apertures.

In some embodiments, apparatus coupled to the sensor 100 is arranged whereby if the amount of RF loss of the cavity member 110 exceeds a prescribed upper threshold value an indication is provided that such an event has occurred. Alternatively or in addition, in some embodiments if the amount of RF loss of the cavity member 110 falls below a prescribed lower threshold value, the apparatus provides an indication that such an event has occurred.

In some embodiments, if the resonant frequency of the cavity member 110 exceeds a prescribed upper threshold the apparatus is arranged to provide an indication that such an event has occurred. Alternatively or in addition, in some embodiments if the resonant frequency of the cavity member 110 falls below a prescribed lower threshold value, the apparatus is arranged to provide an indication that such an event has occurred.

As discussed above, in some embodiments an output is provided corresponding to the resonant frequency of the cavity member 110 and the electromagnetic loss of the cavity member 110. The utility of this feature in some embodiments of the invention may be illustrated with reference to FIG. 3.

Figure 3:
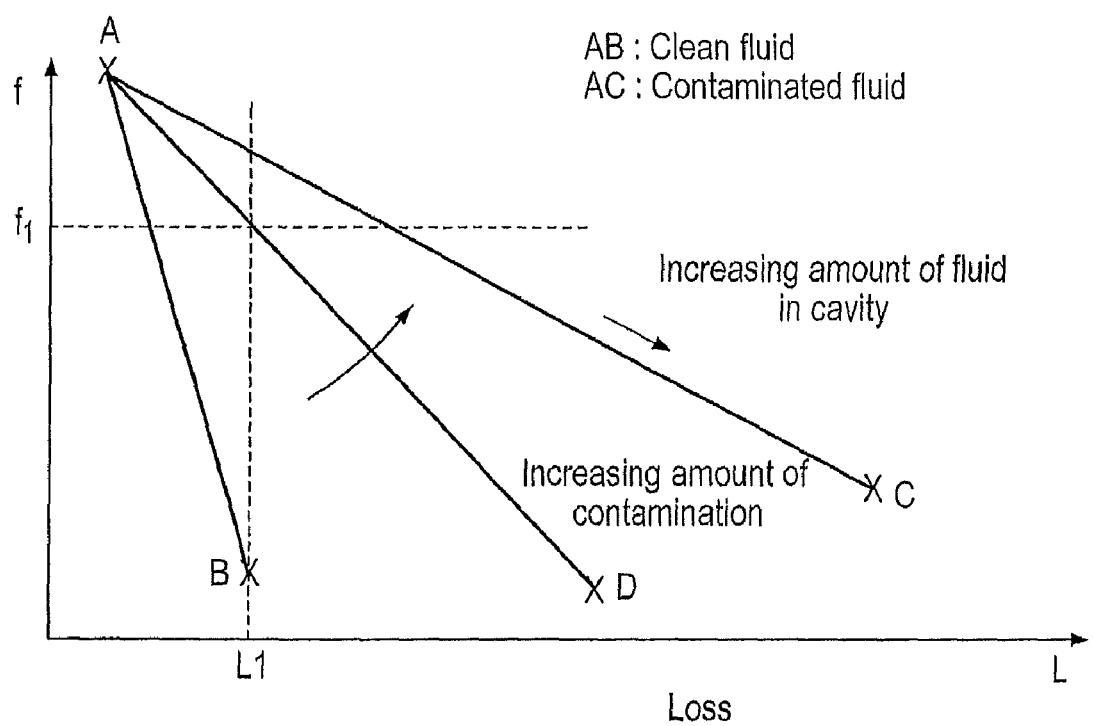
FIG. 3 is a plot of resonant frequency as a function of microwave cavity loss for a cavity member having different amounts of different fluids provided therein.

FIG. 3 is a plot of resonant frequency f of a cavity member 110 as a function of electromagnetic loss L of the cavity member 110. Plotted in FIG. 3 are data (curves AB, AC, AD) corresponding to cavity members 110 having different amounts of a fluid having different amounts of a contaminant contained therein.

Point A corresponds to values of resonant frequency and electromagnetic loss of an empty cavity member 110. Point B corresponds to values of f and L for a cavity member 110 filled with pure (clean) fluid, and line AB corresponds to values of f and L for a cavity member 110 having increasing amounts of clean fluid therein at points of the line in the direction from A to B.

Point C corresponds to a cavity member 110 filled with fluid having a contamination level of a critical value above which the fluid is considered unusable, line AC corresponding to values of f and L of the cavity member 110 having increasing amounts of this fluid therein at points of the line in the direction from A to C.

Point D corresponds to a cavity member 110 filled with fluid of an intermediate contamination level that is less than that of the fluid of point C. Line AD corresponds to values of f and L of a cavity member 110 having increasing amounts of this fluid therein at points of the line in the direction from A to D.

It will be appreciated that if only the value of electromagnetic loss L is known for a given cavity having an unknown quantity of fluid therein, it may not be possible to determine that the contamination level is below the critical value.

It is also to be understood that if only the value of resonant frequency f is known for a given cavity member 110 having an unknown quantity of fluid therein, it may not be possible to determine whether the contamination level is above or below the critical value.

Thus, knowledge of both resonant frequency f and electromagnetic loss L is useful in providing apparatus that can provide an indication whether a property of a fluid is within a prescribed range of parameters regardless of the quantity of fluid present in the cavity member 110.

Similarly, knowledge of both resonant frequency and electromagnetic loss of a cavity member 110 is useful in providing a sensor 100 that can provide an indication of the quantity of fluid present in the cavity regardless of whether a property of the fluid is known to be within a prescribed range of parameters.

Some embodiments of the invention are useful in measuring an amount of fluid such as an amount of a brake fluid that is present in a reservoir. Alternatively or in addition, some embodiments are useful in determining whether a fluid has a concentration of a contaminant therein that is at or above a prescribed concentration.

Figure 4:
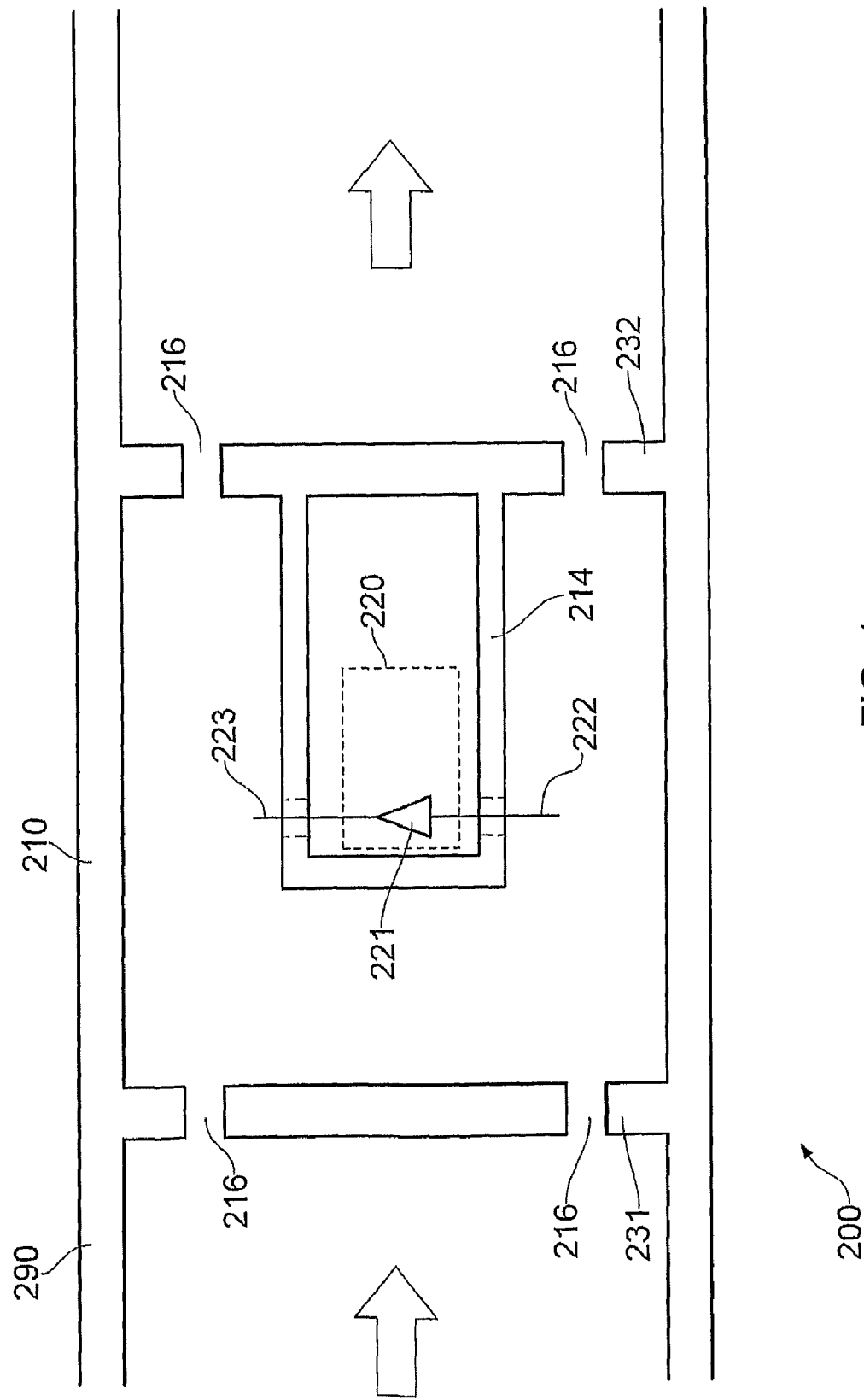
FIG. 4 is a schematic illustration of a pipe having an in-line sensor in the form of a rhumbatron microwave cavity.

FIG. 4 shows an embodiment of the invention in which a sensor 200 is provided having a cavity member 210 provided in a portion of a length of a pipe 290. The cavity member 210 is arranged whereby fluid flowing through the pipe 290 is forced to flow through the cavity member 210.

In the embodiment of FIG. 4 a portion of a length of the pipe 290 provides an outer wall of the cavity member, axially spaced boundaries of the cavity member 210 being provided by plates 231, 232. The plates 231, 232 have apertures 216 formed therein to allow continuous fluid flow through the cavity member 210. As in the case of the embodiment of FIG. 2, in the embodiment of FIG. 4 the apertures 216 are of a size sufficiently small whereby they act as waveguides beyond cut-off, thereby limiting an amount of RF radiation leakage through the apertures 216. In some embodiments the apertures 216 are sufficiently large to allow particles suspended or entrained in the fluid to pass therethrough thereby to prevent blockage of the apertures.

A re-entrant boss portion 214 of the sensor 200 is mounted centrally to one of the plates 232. In the embodiment of FIG. 4 a feedback module 221 is provided within the boss portion 214, the feedback module 221 being electrically coupled to the cavity by means of a pair of stub couplers 222, 223. In the embodiment of FIG. 3 the stub couplers 222, 223 protrude into a volume of the cavity member 210 through which fluid is passed.

In some embodiments, one or both of the stub couplers 222, 223 may be replaced by a loop coupler. In some embodiments, only one coupler is used, as described herein elsewhere. In some embodiments the feedback module 221 is provided externally to the pipe 290. Other arrangements are also useful.

In use, the rhumbatron microwave cavity of FIG. 4 is caused to oscillate as fluid is passed through the pipe. In some embodiments, a controller monitors a resonant frequency of the oscillator circuit and provides an output that corresponds to a value of the resonant frequency. In some embodiments, an output of values corresponding to one or more other parameters is also provided such as electromagnetic loss associated with the cavity.

Figure 5:
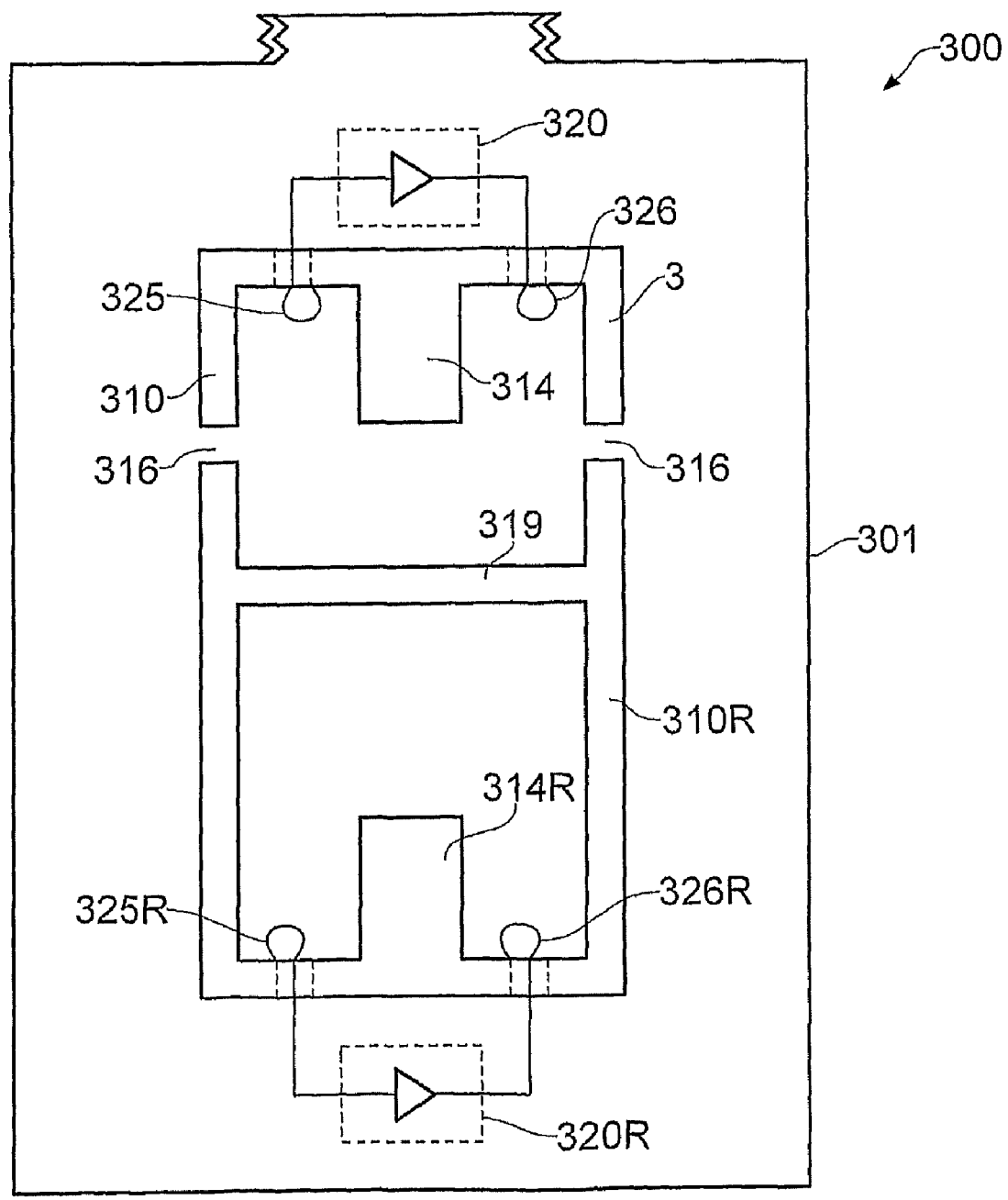
FIG. 5 is a schematic illustration of a sensor having a sensor rhumbatron and a reference rhumbatron.

In some embodiments, a second rhumbatron cavity is provided that is used as a 'reference' cavity. In some embodiments, the reference cavity is not subject to fluid flow therethrough. In some embodiments the second cavity is provided with a reference fluid therein. In use, both cavities are caused to oscillate and a difference between one or more corresponding parameters of respective cavities is measured. FIG. 5 shows such an embodiment in which a sensor 300 is provided having a pair of rhumbatron cavities in mutual juxtaposition.

In some embodiments the cavities are electrically and magnetically isolated from one another such that a value of the resonant frequency or electromagnetic loss of one cavity is substantially unaffected by the value of the resonant frequency or electromagnetic loss of the other cavity.

The sensor 300 is configured whereby one of the cavity members provides a reference cavity member 310R, whilst the other cavity member 310 provides a primary cavity member 310 that is exposed to a fluid under inspection.

The reference cavity member 310R has a re-entrant boss portion 314R and a positive feedback module 320R arranged to cause the cavity member 310R to oscillate at a reference resonant frequency.

Similarly the primary cavity member 310 has a re-entrant boss portion 314 and positive feedback module 320 arranged to cause the primary cavity member 310 to oscillate at a primary resonant frequency.

The positive feedback modules 320, 320R are coupled to cavity members 310, 310R respectively by means of respective pairs of inductive couplers 325, 326 and 325R, 326R as shown in FIG. 5. The inductive couplers in each case pass into the cavity members 310, 310R through apertures formed in a wall of the cavity from which re-entrant boss portions 314, 314R protrude. Other arrangements of inductive couplers are also useful as discussed below. Other types of coupler may be used instead of or in addition to inductive couplers, such as stub couplers.

In the embodiment of FIG. 5 the primary and reference cavity members 310, 310R are formed from a single housing, a baffle member 319 providing a fluid-tight boundary between the two cavity members.

In use, apparatus coupled to the sensor 300 is arranged to compare a value of the resonant frequency and/or electromagnetic loss of the primary and reference cavity members 310, 310R. The apparatus is further arranged to provide an output corresponding to a difference between the respective values of the primary and reference resonant frequencies and/or electromagnetic loss of the primary and reference resonant cavities 310, 310R. In some embodiments of the invention, in the event that a difference falls outside one or more prescribed limits, the apparatus is arranged to generate an alert or other signal.

In some embodiments the reference cavity member 310R is filled with a sample of a fluid of known composition, such as fluid not having contaminants therein. The primary cavity member 310 is filled with a sample of fluid to be inspected and a difference between one or more parameters of each of the primary and reference cavity members 310, 310R is measured. The parameters may correspond to a cavity resonant frequency, a cavity electromagnetic loss, or any other suitable parameter.

If a difference between values of corresponding parameters falls outside of a prescribed range, the apparatus may be configured to provide an indication that such a situation has occurred. For example, if the reference cavity is filled with a sample of substantially contaminant-free fluid, and a difference between one or more corresponding parameters exceeds a prescribed value (corresponding to fluid having a contaminant level above a prescribed critical level), the apparatus may be configured to provide an alert.

In some embodiments the reference fluid corresponds to contaminated fluid. In some embodiments in which this is the case the apparatus may be configured to generate an alert in the event that one or more parameters of the primary cavity member 310 has a value sufficiently close to a corresponding one or more parameters of the reference cavity member 310R. Thus for example as a concentration of contaminants in the primary cavity member 310 approaches that of the reference cavity member 310R a difference between resonant frequencies of the cavity members would be expected to decrease.

In some embodiments of the invention such as those of FIGS. 2, 4 and 5 the re-entrant boss portion 114, 214, 314 has a substantially cylindrical shape. Other shapes are also useful. For example, in some embodiments such as that of FIG. 6(a) the re-entrant boss portion 414 is of a substantially frusto-conical shape, the boss portion 414 being coupled to the cavity portion 412 of cavity member 414 at an apex 414A of the boss portion 414. This has the advantage that an enhanced electric field is provided at opposed longitudinal ends 414A, 414B of the boss portion.

In the embodiment of FIG. 6(b) a cavity member 510 has a re-entrant boss portion 514 having a half dumb-bell shape. Again, an enhanced electric field is provided at opposed longitudinal ends 514A, 514B of the boss portion 514.

FIG. 7 shows an embodiment having a 'slow wave line' re-entrant boss portion 614 in the form of a coiled wire element. A boss portion 614 according to this embodiment has the advantage that an enhancement of the magnetic field associated with a central space of the boss portion is obtained. This permits a cavity member 610 to be provided having a larger magnitude of magnetic field associated with the boss portion than a standard re-entrant boss design.

In some embodiments the slow wave line re-entrant boss portion 614 is formed from a coil of wire having a mark-space ratio of 1 or more. In some embodiments wire of the boss portion 614 is arranged to be freestanding, whilst in some embodiments the wire is wound on a hollow former. Use of a former has the advantage that the structure is less susceptible to mechanical vibrations.

In embodiments having a slow wave line boss portion 614 the region of high magnetic field is typically inside the coil.

FIG. 8 shows an embodiment of the invention in which a cavity member 710 of a sensor 700 is provided with a hollow coaxial tuning slug 750. The slug 750 is arranged to be coaxial with a re-entrant boss portion 714 of the cavity member 710 and axially displaceable with respect thereto. Changing the axial position of the slug 750 allows a resonant frequency of oscillation of the cavity member 710 to be changed.

In some embodiments in which two cavities are provided, such as a primary cavity and a reference cavity, at least one of the cavities may be provided with a tuning slug 750. In some embodiments, in use the position of the slug 750 is adjusted such that a resonant frequency and/or an electromagnetic loss of the primary and reference cavities are substantially equal when filled with a quantity of a similar fluid, such as a fluid of the type to be measured having substantially no target measurand therein.

Alternatively the position of the slug 750 may be adjusted such that a resonant frequency and/or an electromagnetic loss of the primary and reference cavities are substantially equal when each is filled with a prescribed quantity of a different respective prescribed fluid, such as a sample of a fluid having substantially no target measurand therein, and a sample of the same fluid having a critical concentration of target measurand therein. In use, when a difference between resonant frequencies of the cavities falls below a critical value, it may be concluded that a concentration of target measurand (e.g. a contaminant) in the primary cavity member has approached or exceeded a critical concentration.

In some embodiments the reference cavity is filled with a sample of a fluid of the type that is to be inspected, the sample in the reference cavity having a critical concentration of a target measurand therein. The resonant frequencies of the cavities are then set to be substantially equal by adjustment of the position of one or both slugs.

In use, a difference in resonant frequency and/or electromagnetic loss of the primary and reference cavities is measured. It is to be understood that in this case if the difference between the respective measurements exceeds a prescribed value, it may be concluded that a concentration of target measurand in the primary cavity is comparable to that within the reference cavity.

FIG. 9 shows an embodiment in which a cavity member 810 having a re-entrant boss portion 814 is provided wherein a wall of the cavity member 810 has a screw element 850 provided therein. The screw element 850 is adjustable whereby an extent to which the screw element 850 protrudes into an internal volume of the cavity member 810 may be varied. This has the effect that a value of the resonant frequency and/or electromagnetic loss of the cavity member 810 may be tuned to a required value.

FIG. 10 shows a rhumbatron microwave cavity sensor 900 having a stub coupler 922 protruding into an inner volume of a cavity portion 912 of cavity member 910. In its simplest form the stub coupler is a substantially straight conducting element that is arranged to pass through an aperture 927 formed in a wall of the cavity portion 912. The stub coupler 922 is arranged to couple to electric field lines established in the cavity member 910 when the cavity member 910 is excited with RF radiation.

In the embodiment of FIG. 10 the stub coupler 922 is inserted through an aperture 927 formed in a portion of the wall facing a free end 914' of re-entrant boss portion 914 of the cavity member 910. Other positions of apertures 927 are also useful, such as in a wall of boss member 914, at or near the free end 914' of boss member 914 or any other suitable location.

In some embodiments an inductive coupler (or 'loop coupler') is inserted through aperture 927 of the cavity member 910 of FIG. 10. An inductive coupler 1025 is illustrated in FIG. 11, the inductive coupler being arranged to pass through an aperture 1027 formed in a wall of cavity member 1010. In the embodiment shown in FIG. 11 the aperture 1027 is formed in a basal wall 1010B being a portion of the wall of cavity member 1010 from which re-entrant boss portion 1014 of cavity member 1010 protrudes.

The inductive coupler 1025 is in the form of a wire element similar to that of the stub coupler of FIG. 10, a primary difference being that a free end of the coupler of FIG. 11 is curved to form at least a portion of a loop and coupled to the wall of the cavity member 1010. The inductive coupler 1025 is arranged to couple to magnetic flux lines established in the cavity member 1010 when the cavity member 1010 is excited with RF radiation.

It is to be understood that the position of couplers 922, 1025 may be reversed, i.e. stub coupler 922 may be substituted for inductive coupler 1027 of FIG. 10 and FIG. 11 respectively and inductive coupler 1027 may be substituted for stub coupler 922. Other locations of the wall of the cavity member 910, 1010 and/or re-entrant boss portion 914 for placement of the couplers are also useful.

However, it is to be understood that in some embodiments stub couplers are advantageously positioned at locations where relatively large changes in electric field strength occur during oscillation of the sensor 900, whilst inductive couplers are advantageously positioned at locations where relatively large changes in magnetic field strength occur during oscillation of the sensor 900.

FIG. 17 illustrates an arrangement of magnetic flux lines in a rhumbatron cavity member 1710 suitable for use in some embodiments of the invention. FIG. 17(a) is a cross-sectional view of the cavity member 1710 whilst FIG. 17(b) is a plan view of the cavity member 1710.

A snapshot of magnetic flux lines established within the cavity member 1710 when oscillating at RF frequencies are shown in FIG. 17(a) and (b). In FIG. 17(a) magnetic flux lines travelling in a direction into the page are represented by arrow tails $H_t$ whilst magnetic flux lines travelling in a direction out of the page are represented by arrowheads $H_h$. In FIG. 17(b), arrows H show a direction of magnetic flux lines within the cavity member 1710 as viewed in plan view.

Arrow A of FIG. 17(a) shows a direction in which magnetic field strength within the internal volume of the cavity member 1710 increases. It is to be understood that higher magnetic field strengths are established in a portion of an internal volume of the cavity member 1710 in the region surrounding a base portion 1714B of the boss portion 1714 that is coupled to basal wall 1710B. As can be seen from FIG. 17 the base portion 1714B of boss portion 1714 is axially displaced from free end 1714' of the boss portion.

Thus, in embodiments in which inductive couplers are used the couplers are generally provided in the region proximate the base portion 1714B (see for example FIG. 5, 11, 12, 14, 16).

FIG. 18 illustrates electric field lines (represented by arrows E) established within the cavity member 1710 when oscillating at RF frequencies. A direction in which electric field strength within the internal volume of the cavity member 1710 increases is shown by arrow C.

In the cavity members illustrated in the figures, the highest electric fields are generally established in regions of the internal volume of the cavity member axially displaced away from the boss portion 1714 and towards a wall of the cavity portion 1710A facing free end 1714' of boss portion 1714. Relatively low magnetic fields are established in this region.

Similarly, the lowest electric fields are generally established in regions of the internal volume towards a basal wall 1710B of the cavity member, being a wall from which the boss portion 1714 projects. (The boss portions of the cavity members illustrated in the figures may be considered to 'project' or 'protrude' into an internal volume of the cavity portion in each case).

In some embodiments, cavity members 1110 (FIG. 12) are provided in which 'retreated' couplers are employed. By 'retreated' coupler is meant a coupler provided in an aperture 1127A, 1127B that does not protrude into a volume of the cavity member 1110 substantially beyond a plane P (FIG. 12) of an inner surface of a wall of the cavity member 1110 in which the aperture 1127A, 1127B has been formed. It is to be understood that withdrawal of a coupler from an internal volume of the cavity member 1110 (FIG. 12) into an aperture 1127A, 1127B (FIG. 12) reduces a coupling strength of a coupler to an electric and/or magnetic field present in the cavity member 1110.

In some embodiments a single stub or inductive coupler may be used to excite a cavity member. FIG. 13 shows an embodiment in which a single stub coupler 1222 is provided through an aperture 1227A formed in a portion of a wall of a cavity portion 1212 facing re-entrant boss portion 1214 of the cavity member 1210. It is to be understood that other locations of the stub coupler 1222 are also useful such as within boss portion 1214 which is hollow in some embodiments of the invention (see e.g. FIG. 2).

A negative resistance element 1221 is provided, having a terminal 1220A and a terminal 1220B, terminal 1220A being connected to the stub coupler 1222 and terminal 1220B being coupled to the cavity wall close to aperture 1227A through which stub coupler 1222 protrudes.

In embodiments in which a single stub or loop coupler is used with a negative resistance element 1221 to excite a cavity, the negative resistance element 1221 may be provided by a device exhibiting negative resistance such as a Gunn diode, a tunnel diode or any other suitable negative resistance device. In some embodiments of the invention the negative resistance element 1221 is provided together with appropriate ancillary components for biasing the negative resistance device and decoupling DC voltages from AC voltages. An example of a negative resistance element 1221 having a bias control arrangement is shown in FIG. 13A.

In some embodiments the negative resistance element 1221 is alternatively provided by a gain block to which feedback is applied (see e.g. FIG. 13B). FIG. 13B shows an embodiment in which the gain block is provided by an amplifier having a positive electrical feedback arrangement.

FIG. 14 shows a corresponding cavity member 1310 having a negative resistance element 1321. An inductive coupler 1325 is disposed to pass through an aperture 1327B formed in a portion of a wall of cavity member 1310, the portion being a portion of a wall from which re-entrant boss portion 1314 projects. It is to be understood that other locations of aperture 1327B are also useful.

As in the case of the coupler of FIG. 13, the coupler of FIG. 14 is coupled to a terminal 1320A of negative resistance element 1321 whilst terminal 1320B of the negative resistance element 1321 is coupled to the wall of the cavity member 1310 close to aperture 1327B.

It is to be understood that the negative resistance element 1321 of the embodiment of FIG. 14 may alternatively be provided by a negative resistance element as shown FIG. 13A or FIG. 13B.

FIG. 15 shows a cavity member 1410 in which a pair of stub couplers 1422, 1423 are provided through apertures formed in a portion 1412A of a wall of cavity portion 1412 facing a free end 1414' of re-entrant boss portion 1414. The couplers 1422, 1423 are coupled respectively to an input and an output of a positive feedback module 1420.

It is to be understood that the stub couplers 1422, 1423 of the embodiment of FIG. 15 may be located in the same locations as stub couplers 222, 223 of the embodiment of FIG. 4. This has the advantage that the stubs are screened from one another. Consequently parasitic oscillation due to stray coupling between the stubs is less likely to occur.

FIG. 16(a) shows a cavity member 1610 having a positive feedback module 1620 that has an input coupled to the cavity member 1610 by means of a stub coupler 1622 an output coupled to the cavity member 1610 by means of an inductive coupler 1625. The stub and inductive couplers are disposed to pass through apertures 1627A, 1627B respectively formed in the re-entrant boss portion 1614 at positions axially displaced from one another with respect to a longitudinal axis L of re-entrant boss portion 1614.

The arrangement of FIG. 16(b) is also suitable for use in some embodiments of the invention and has a cavity member 1610 substantially identical to that of FIG. 16(a). The arrangement differs from that of FIG. 16(a) in that positive feedback module 1620 in the arrangement of FIG. 16(b) has an input 1620A coupled to inductive coupler 1625 and an output 1620B coupled to a stub coupler 1622.

In the cavity members of FIG. 16 aperture 1627A through which the stub coupler 1622 passes is displaced closer to a free end 1614' of the boss portion 1614 than aperture 1627B through which inductive coupler 1625 passes.

In general it is preferable but not essential that inductive couplers are employed in circumstances where a coupler is required to be provided in a region of an internal volume of a cavity member 1610 in which relatively high magnetic fields are established, as opposed to regions of the internal volume in which relatively low magnetic fields are established. Similarly, it is preferable but not essential that stub couplers are employed in circumstances where a coupler is required to be provided in a region of an internal volume of a cavity member 1610 in which relatively high electric fields are established, as opposed to regions of the internal volume in which relatively low electric fields are established.

In some embodiments of the invention such as that of FIG. 19 fluid is introduced into the cavity portion 1810 by means of a tube 1890 that is connected between a fluid inlet and a fluid outlet of the cavity portion. In some preferred embodiments the tube is formed from an electrically insulating low dielectric loss material such as PTFE (e.g. Teflon™) or a glass material that is passed through the cavity through which the liquid is flowed. The dielectric loss of the tube material is chosen to be sufficiently low that it does not significantly depress the quality factor of the cavity.

As a consequence of using a tube instead of filling the entire cavity portion 1810 with fluid, a relatively small but known quantity of fluid is present in the cavity (assuming no gas bubbles are present in the tube).

Such embodiments are particularly useful where liquids of relatively high loss and/or relatively high dielectric constant are used since a risk that oscillation of the cavity member 1810 is terminated upon introduction of the liquid into the tube 1890 or the resonant frequency shifted beyond the range in which electronic devices associated with the sensor function satisfactorily is reduced.

In some embodiments of the invention a modulated DC magnetic field is applied to the cavity member to induce Zeeman splitting in the measurand of an amount that is equal to the cavity frequency, thereby increasing sensitivity of the cavity sensor to the measurand. In some embodiments the DC magnetic field has a magnitude of about 0.1 to 2 T. Such embodiments are particularly useful in applications such as the detection of magnetic nanoparticles that have been used to label cells or biological molecules in flowing blood or other medical fluid.

Some embodiments of the invention are useful in detecting moisture in a fluid such as moisture in liquid fuel, automatic transmission fluid (ATF), brake fluid or oil. In some embodiments a sensor is provided in a motor vehicle. In some embodiments a moisture sensor is coupled to an oil line, a fuel line or a brake line and fluid passing through the sensor is inspected to determine whether an amount of moisture present in the liquid exceeds a critical amount.

Embodiments of the invention are useful in detecting a state of other fluids and solids. For example, in some embodiments a sensor is used to detect an amount of liquid in an object such as a contact lens.

Apparatus as claimed in any preceding claim arranged to detect the presence of at least one selected from amongst liquid helium, liquid nitrogen, water, a Van Vleck paramagnet, a Curie Law paramagnet, a diamagnet, a thin ferromagnetic film or multilayer film by ferromagnetic resonance, a giant magneto-resistive film or multilayer by ferromagnetic resonance, a ferromagnetic particle or assembly of particles, a superconductor and an electron spin resonance system.

In some embodiments apparatus is arranged to detect, size and characterize a ferromagnetic particle or assembly of paramagnetic particles by ferromagnetic resonance and to allow observation of the spin-wave spectrum.

In some embodiments apparatus is arranged to detect and characterize a superconductor by sweeping a magnetic field applied to the cavity and observing the cavity properties. Detection of the superconductor makes use of the modified RF and microwave absorption exhibited by a superconducting material in zero applied magnetic field.

In some embodiments apparatus is arranged to detect and characterize an electron spin resonance system.

In some embodiments apparatus is arranged to detect and characterize an enhanced nuclear resonance system.

In some embodiments apparatus is arranged to detect the Curie point in a ferromagnetic intruder into a cavity of the apparatus.

In some embodiments apparatus is arranged to detect the Neel point in an anti-ferromagnetic intruder into a cavity of the apparatus.

In some embodiments apparatus is arranged to detect boiling in liquids

In some embodiments apparatus is arranged to detect and monitor the progress of a chemical reaction—for example curing of epoxy resin.

In some embodiments apparatus is arranged to detect a state of hydration of a material—for example grain or contact lenses In some embodiments apparatus is arranged to detect and measure applied magnetic field via its effect on a superconductor, a giant magneto-resistance (GMR) system, a Curie law paramagnet or an ordered magnetic material.

In some embodiments apparatus is arranged to measure applied magnetic field by measuring the electronic spin resonance in DPPH diphenylpicrylhydrazyl.

In some embodiments apparatus is arranged to detect carbon in engine oil.

In some embodiments apparatus is arranged to detect metal filings in automatic transmission fluid (ATF) or engine oil via frequency shift, ferromagnetic resonance or observation of the spin-wave spectrum.

In some embodiments apparatus is arranged to detect degradation of corrosion protection in glycol-based or other antifreeze.

The electronics of apparatus according to some embodiments of the invention is designed to allow the cavity to operate at temperatures between 4 and 300 K In some embodiments mechanical and/or electrical frequency modulation may be used as a means of modulating and extracting a required signal from the oscillator circuit with an enhanced signal to noise ratio.

Apparatus may be used in combination with an optical beam that penetrates and traverses the cavity thereby to provide further information about a sample. In some embodiments, the optical beam is used to enhance device sensitivity to a target measurand by using optical pumping to change a susceptibility or a quantum level population of the measurand.

Imaging of intruded material may be achieved by imposing external magnetic fields and field gradients in some embodiments of the invention.

In some embodiments apparatus is used for ESR spin-echo spectroscopy. In some embodiments magnetic fields are enhanced by throttling a base portion of the re-entrant boss portion of the cavity member.

In some embodiments a rhumbatron re-entrant microwave cavity is used to monitor the condition and particulate content of ATF in which the cavity is placed in line with the ATF flow to the radiator heat exchanger and the ATF flows axially through the rhumbatron being introduced/removed via holes in the cavity that pass fluid but function as waveguides in cut-off at the cavity frequency thereby ensuring microwave electrical isolation of the cavity from its environment.

In some embodiments a rhumbatron re-entrant microwave cavity is used to monitor the condition and particulate content of automotive engine oil in which the cavity is placed in line with the bypass or full-flow oil flow to the oil-cooler heat exchanger and the oil flows axially through the rhumbatron being introduced/removed via holes in the cavity, the holes being arranged as described above.

In some embodiments a rhumbatron re-entrant microwave cavity is used to monitor the condition, degradation, water content and particulate content of brake fluid in which the cavity is immersed in the vehicle's brake-fluid reservoir and the fluid is introduced and removed via holes in the cavity, the holes being arranged as described above.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Thus for example it is to be understood that location of couplers and the type of coupler at a given location may be varied as required, locations and/or types of couplers used in one embodiment being applicable to another embodiment unless explicitly stated not to be so applicable.

The invention claimed is:

1. An apparatus comprising:
   a radio frequency (RF) Robinson oscillator comprising:
      a resonator comprising a sensor rhumbatron, the sensor rhumbatron comprising a cavity member, the cavity member having a re-entrant boss member, the re-entrant boss member being arranged to project into a cavity portion of the cavity member;
      a feedback element arranged within the boss member to provide positive radio frequency (RF) feedback to the cavity member thereby to increase a quality factor Q of the cavity member, the feedback element having first and second terminals coupled to the cavity member, the apparatus being operable to cause the oscillator to oscillate at a resonant frequency; and
      an output arranged to provide a signal that varies according to a value of at least one electrical parameter of the oscillator, said at least one electrical parameter being selected from amongst an electromagnetic loss and a resonant frequency of the cavity member.

2. An apparatus comprising:
   a radio frequency (RF) Robinson oscillator comprising:
      a resonator comprising a sensor rhumbatron having a cavity member, the cavity member having a re-entrant boss member arranged to project into a cavity portion of the cavity member;
      a negative resistance element arranged within the boss member and configured to exhibit negative resistance between first and second terminals of the element, the first and second terminals being coupled to the cavity member, the apparatus being operable to cause the oscillator to oscillate at a resonant frequency; and
      an output arranged to provide a signal that varies according to a value of at least one electrical parameter of the oscillator, said at least one parameter being selected from amongst an electromagnetic loss and a resonant frequency of the cavity member.

3. The apparatus as claimed in claim 2, wherein the first and second terminals are coupled to the boss member and cavity member, respectively.

4. The apparatus as claimed in claim 3, wherein the first and second terminals of the negative resistance element are coupled to the boss member and cavity member respectively at respective first and second positions whereby the impedance of the negative resistance element corresponds to an impedance of the cavity member between the first and second positions.

5. The apparatus as claimed in claim 3, wherein the negative resistance element comprises a Gunn diode or a tunnel diode.

6. The apparatus as claimed in claim 5, wherein the negative resistance element comprises a tunnel diode and wherein the tunnel diode is an Esaki diode.

7. The apparatus as claimed in claim 3, wherein the negative resistance element comprises a gain element arranged such that positive feedback is applied to an input thereof from an output thereof.

8. The apparatus as claimed in claim 2, further comprising a means for introducing a target measurand into an interior of the cavity member.

9. The apparatus as claimed in claim 2, wherein the cavity member is provided with a fluid inlet and a fluid outlet, the apparatus being arranged whereby a fluid flow-path is provided through at least a portion of an interior of the cavity member between the fluid inlet and the fluid outlet.

10. An apparatus comprising:
    a radio frequency (RF) Robinson oscillator comprising:
       a resonator comprising a sensor rhumbatron having a cavity member, the cavity member having a re-entrant boss member arranged to project into a cavity portion of the cavity member,
       an output arranged to provide a signal that varies according to a value of at least one electrical parameter of the oscillator, said at least one parameter being selected from among an electromagnetic loss and a resonant frequency,
       wherein the cavity member is provided with a fluid inlet and a fluid outlet, the apparatus being arranged whereby a fluid flow-path is provided through at least a portion of an interior of the cavity member between the fluid inlet and the fluid outlet; and
       a feedback element arranged within the boss member to provide positive radio frequency (RF) feedback to the cavity member thereby to increase a quality factor Q of the cavity member, the feedback element having first and second terminals coupled to the cavity member, the apparatus being operable to cause the oscillator to oscillate at a resonant frequency of the cavity member.

11. The apparatus as claimed in claim 10 configured whereby the first cavity member may be substantially filled with a fluid by forcing fluid through the first cavity member from the fluid inlet to the fluid outlet.

12. The apparatus as claimed in claim 10, wherein the fluid inlet and the fluid outlet are each provided by an aperture in a wall of the cavity member, a diameter of the aperture being arranged to be sufficiently small whereby the aperture provides a waveguide configured to function in a cut-off condition when the sensor rhumbatron is excited in use.

13. The apparatus as claimed in claim 10 arranged whereby a direction of flow of fluid through the cavity member from the inlet aperture to the outlet aperture is substantially parallel to a longitudinal axis of the boss member.

14. The apparatus as claimed in claim 10 arranged wherein fluid flowing through the cavity member from the inlet to the outlet is confined to a tube member provided between the inlet and the outlet, the tube member having a fluid capacity in a volume of the tube member between the inlet and outlet that is less than a fluid capacity of the cavity member.

15. The apparatus as claimed in claim 10 further comprising a reference RF oscillator, the reference RF oscillator having a reference resonator comprising a reference rhumbatron, the reference rhumbatron having a reference cavity member, the reference cavity member having a reference fluid provided therein, the reference oscillator being operable to oscillate at a reference resonant frequency.

16. The apparatus as claimed in claim 15 further configured to provide an output corresponding to at least one selected from among a resonant frequency of the reference rhumbatron, an electromagnetic loss of the reference rhumbatron, a difference between a resonant frequency of the sensor oscillator and a resonant frequency of the reference oscillator, and a difference between an electromagnetic loss of the cavity member of the sensor rhumbatron and an electromagnetic loss of the cavity member of the reference rhumbatron.

17. The apparatus as claimed in claim 10, wherein a magnetic field is applied to the cavity to enhance sensitivity to the measurand.

18. The apparatus as claimed in claim 10, wherein the first and second terminals are coupled to one another, the first and second terminals being coupled to the rhumbatron by means of a single coupler, preferably a single loop coupler or a single stub coupler.

19. The apparatus as claimed in claim 10, wherein the first terminal is coupled to the rhumbatron by means of at least one selected from among a loop coupler and a stub coupler and the second terminal is coupled to the rhumbatron by means of at least one selected from among a loop coupler and a stub coupler.

20. The apparatus as claimed in claim 10 arranged to detect the presence of at least one selected from among liquid helium, liquid nitrogen, water, a Van Vleck paramagnet, a Curie Law paramagnet, a diamagnet, a thin ferromagnetic film or multilayer film by ferromagnetic resonance, a giant magneto resistive film or multilayer by ferromagnetic resonance, a ferromagnetic particle or assembly of particles, a superconductor and an electron spin resonance system.

* * * * *